(12) United States Patent
Lang

(10) Patent No.: US 7,696,160 B2
(45) Date of Patent: Apr. 13, 2010

(54) COMPOSITIONS USEFUL FOR AND METHODS OF MODULATING ANGIOGENESIS

(75) Inventor: Richard Lang, Loveland, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 194 days.

(21) Appl. No.: 12/074,853

(22) Filed: Mar. 6, 2008

(65) Prior Publication Data

US 2009/0036373 A1 Feb. 5, 2009

Related U.S. Application Data

(63) Continuation of application No. PCT/US2006/034926, filed on Sep. 8, 2006.

(60) Provisional application No. 60/714,970, filed on Sep. 8, 2005.

(51) Int. Cl.
*C07K 14/00* (2006.01)
(52) U.S. Cl. .......................... 514/2; 530/350
(58) Field of Classification Search ........................ None
See application file for complete search history.

(56) References Cited

U.S. PATENT DOCUMENTS

| | | | |
|---|---|---|---|
| 5,650,490 A | 7/1997 | Davis | |
| 5,851,984 A | 12/1998 | Matthews | |
| 6,159,462 A | 12/2000 | Matthews | |
| 6,432,667 B1 | 8/2002 | Valenzuela | |
| 6,653,448 B1 | 11/2003 | Vernet | |
| 6,656,461 B1 | 12/2003 | D'Armiento | |
| 2004/0023864 A1 | 2/2004 | Roczniak | |
| 2004/0247593 A1 | 12/2004 | He | |

FOREIGN PATENT DOCUMENTS

| WO | WO 02057496 A2 | 7/2002 |
|---|---|---|
| WO | WO 03/004045 A2 | 1/2003 |
| WO | WO 2004032838 A2 | 4/2004 |
| WO | WO 2005033048 A2 | 4/2005 |

OTHER PUBLICATIONS

PCT US06/34926, Feb. 16, 2007, Lang, ISR-box V, p. 8.
PCT US06/34926, Apr. 7, 2009, Lang, Prelim. Report on Patentability.
Davis, "Angiopoietins have distinct modular domains essential for receptor binding, dimerization, and superclustering", Nature Structural Biology, Sep. 2, 2002,p. 38-45, 10-1.
Huguet, "Differential Expression of Human Wnt Genes 2, 3, 4, and 7b in human breast cell lines and normal and disease states of human breast tissue," Cancer Research, May 15, 1994, 2615-2621, vol. 54.
Lobov, "WNT7b mediates macrophage induced programmed cell death in patterning of the vasculature", Nature, Sep. 15, 2005, 417-421, vol. 437(7057).
Maisonpierre, "Angiopoietin2 a natural antagonist for Tie-2 that disrupts in vivo angiogenesis", Science, Jul. 4, 1997, p. 55-60, vol. 57.
Tanaka, "Biologic significance of angiopoietin-2 expression in human hepatocellular carcinoma", Journal of Clinical Investigation, Feb. 1999, 341-345, v103-3.
Gray, Henry. Anatomy of the Human Body On-line Edition. May 2000. Bartleby.com Section V. Angiology.
Wang. "Wnt7b activates canonical signaling in epithelial and vascular smooth muscle cells through interactions with Fzd1, Fzd10, and LRP5", Molecular Cell Biology. Jun. 2005 5022-5030, 25-12.
Frietas. "Arteriovenous Microcirculation", Nanomedicine, vol. I:Basic Capabilities, Feb. 19, 2003.
Robitaille. "Mutant frizzled-4 disrupts retinal angiogenesis in familial exudative vitreoretinotherapy," Nature Genetics, Sep. 2002, 326-330, v.32.

*Primary Examiner*—Karen Cochrane Carlson
(74) *Attorney, Agent, or Firm*—Taft Stettinius & Hollister LLP

(57) ABSTRACT

Compositions and methods for treating subjects with disorders characterized by aberrant vascular endothelial cell growth are provided. The compositions comprise agents that are combinations of a Wnt pathway stimulator component and a Tie2 pathway repressor component. Particularly useful Wnt pathway stimulators include, but are not limited to, Wnt7b-like molecules. Particularly useful Tie2 pathway repressor components include, but are not limited to, Ang2-like molecules. The methods allow for modulation of vascular endothelial cells, vascular endothelial cell vessels, capillary bed development, and angiogenesis.

23 Claims, 15 Drawing Sheets

COMPOSITIONS USEFUL FOR AND METHODS OF MODULATING ANGIOGENESIS

CROSS-REFERENCE TO RELATED APPLICATIONS

This application is a continuation of and claims priority to and benefit of PCT US06/34926, filed on Sep. 8, 2006, and U.S. Provisional Patent Application No. 60/714,970, filed on Sep. 8, 2005, which are incorporated herein by reference in their entirety.

FIELD OF THE INVENTION

The invention relates to the field of modulation of vascular endothelial cell vessels and angiogenesis.

BACKGROUND OF THE INVENTION

Macrophages have a critical role in inflammatory and immune responses through their ability to recognize and engulf apoptotic cells (Savill et al. (2002) *Nature Rev. Immunol.* 2:965-975, herein incorporated by reference in its entirety). It is widely believed that macrophage involvement in programmed cell death occurs after the apoptotic event in response to membrane-tethered or soluble "eat-me" signals from dead and dying cells. However, in some circumstances phagocytes actively induce programmed cell death. In mice, macrophages are required for the programmed regression of temporary capillary networks within the developing eye (Lang, R. A. & Bishop, M. J. (1993) *Cell* 74:453-462 and Diez-Roux, G. & Lang, R. A. (1997) *Development* 124:3633-3638, herein incorporated by reference in their entirety). The mechanisms governing macrophage involvement in programmed cell death have not been clarified.

The Wingless (Wnt) signaling pathway has a crucial function in developmental cell fate decisions, and when aberrantly activated, in the development of cancer (Bienz, M & Clevers, H. (2000) *Cell* 103:311-30). In vertebrates, the canonical Wnt response requires a receptor complex comprising the co-receptor Lrp5 or Lrp6 and a multi-transmembrane pass receptor of the frizzled family. When activated by a Wnt ligand, this complex initiates a cascade of events that culminates in stabilization of β-catenin, its association with Lef/Tcf family of transcription factors and the regulation of target genes including some that stimulate cell cycle entry (see Nusse (1999) *Trends Genet* 15:1-3; Bienz & Clevers (2000) *Cell* 103:311-320; He et al. (2004) *Development* 131:1663-1677; Perrimon, N. (1996) *Cell* 86:513-516; Behrens et al. (1996) *Nature* 382:638-642, herein incorporated by reference in their entirety).

The Wnt gene family includes at least ten genes that encode structurally related secreted glycoproteins. Members of the Wnt family are reported to be regulators of mammary cell growth and differentiation. For example, dysregulation of Wnt signaling has been reported to cause developmental defects and to be implicated in the genesis of several human cancers. Overexpression of Wnt-7b proteins can result in cellular transformation of C57MG cells. Higher Wnt7b expression levels have also been reported in superficial bladder cancer cells as compared to invasive bladder cancer cells. These results suggest that the Wnt7b polypeptide is involved in the early events of bladder tumorigenesis (U.S. Pat. No. 6,653,448 B1, herein incorporated by reference in its entirety).

Angiopoietins are a family of vascular growth factors that collaborate with members of the vascular endothelial growth factor family to regulate vascular and lymphatic vessel growth, acting via the endothelial receptor tyrosine kinase Tie 2. Although angiopoietin-1 seems to be an obligate activator of the Tie2 receptor, angiopoietin-2 (Ang2) seems to have context specific effects, activating this receptor on some cells while blocking Tie2 activation on other cells or under other conditions. Ang2 is a context-dependent agonist/antagonist of Tie2 and displays a similar multimerization state to angiopoietin-1. See Davis et al. (2003) *Nature Structural Biology* 10:38-44, herein incorporated by reference in its entirety.

Thus, a mechanistic assessment of Wnt7b and Ang2's in vivo role is desirable. It is of importance to develop methods of modulating vascular endothelial cell vessel formation. It is of further importance to develop methods of modulating Wnt7b expression.

SUMMARY OF THE INVENTION

Compositions useful for and methods of modulating a vascular endothelial cell vessel are provided. The inventions are based on the novel discovery that activation of the canonical Wingless (Wnt) signaling pathway and repression of the Tie2 signaling pathway induces apoptosis or programmed cell death in vascular endothelial cells. This discovery counters the widely held notion that Wnt7b facilitates the early events of tumorigenesis. Exposure of a vascular endothelial cell to a Wnt pathway stimulator, such as Wnt7b, and a Tie2 pathway repressor, such as Angiopoietin-2 (Ang2), induces programmed cell death.

Compositions of the invention include a vascular endothelial cell vessel modulating compound comprising a Wnt pathway stimulator and a Tie2 pathway repressor. In an aspect of the invention, the Wnt pathway stimulator is a Wnt7b-like molecule. In an aspect of the invention, the Wnt7b-like molecule is Wnt7b or a Wnt7b fragment or variant thereof. In an aspect of the invention, the Tie2 pathway repressor is an Ang2-like molecule. In an aspect of the invention, the Ang2-like molecule is Ang2 or an Ang2 fragment or variant thereof. In an aspect of the invention, the Wnt pathway stimulator is a Wnt7b-like molecule and the Tie2 pathway repressor is an Ang2-like molecule. When administered, the compositions of the invention find use in modulating angiogenesis, vascular endothelial cell vessels, and apoptosis of a vascular endothelial cell. In aspects of the methods of modulating a vascular endothelial cell vessel, the vascular endothelial cell vessel regresses. In aspects of the methods of modulating apoptosis of a vascular endothelial cell, the vascular endothelial cell undergoes apoptosis.

An embodiment of the invention provides methods of modulating a vascular endothelial cell vessel comprising the step of administering a vascular endothelial cell vessel modulating compound. In an aspect of the method, the vascular endothelial cell vessel regresses. In an aspect of the method, a vascular endothelial cell of the vascular endothelial cell vessel undergoes apoptosis.

An embodiment of the invention provides methods of modulating an angiogenic-related disorder. The methods comprise the steps of identifying a subject exhibiting an angiogenic related disorder and administering a therapeutically effective amount of a compound comprising a Wnt pathway stimulator and a Tie2 pathway repressor to the subject. In an aspect of the invention, the angiogenic related disorder is selected from the group consisting of, but not limited to, ocular angiogenic disorders and hyperproliferative disorders. In an aspect of the invention the Wnt pathway stimulator is a Wnt7b-like molecule and the Tie2 pathway repressor is an Ang2-like molecule. In an aspect of the invention the angiogenic related disorder is vascular endothelial cell vessel-related disorder. In an embodiment a vascular endothelial cell vessel regresses. In an aspect of the method, a vascular endothelial cell of the vascular endothelial cell vessel undergoes apoptosis.

An embodiment of the invention provides methods of modulating capillary bed development. The methods comprise the step of administering a vascular endothelial cell vessel modulating compound comprising a Wnt pathway stimulator and a Tie2 pathway repressor to a subject.

Another embodiment of the invention provides methods of modulating a vascular endothelial cell vessel-related disorder. The methods comprise the step of administering a Wnt7b expression modulating agent.

Panels E-H present micrographs of hyaloid vessel preparations stained with Hoechst 33258. The vessels in panels E and F were obtained from wild-type mice at ages P3 and P8. The vessels in panels G and H were obtained from PU.1$^{-/-}$ mice at ages P3 and P8. Panels E-H are at 50× magnification.

Panel I presents a graphical summary of hyaloid vessel number (y-axis) in P8 mice. Column 1 indicates the mean number of hyaloid vessels in wild-type mice; column 2 indicates the mean number of hyaloid vessels in PU.1$^{+/-}$ mice; column 3 indicates the mean number of hyaloid vessels in PU.1$^{-/-}$ mice. Error bars indicate standard error.

Figure 1A:
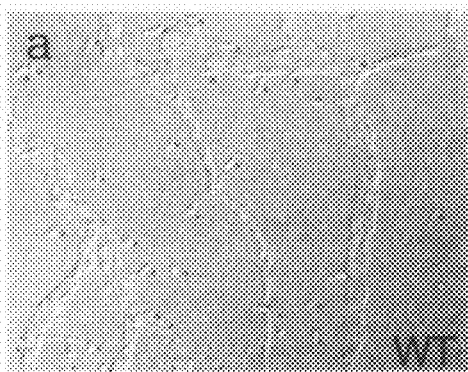
FIG. 1 presents an assessment of the effect of macrophage cells on hyaloid vessel regression. Details of the experiment are presented elsewhere herein. Panels A-D present micrographs of hyaloid vessel preparations from wild-type (Panels A and C) and PU.1$^{-/-}$ (Panels B and D) mice at P5. The micrographs in Panels A and B indicate results obtained from differential interference contrast illumination of the preparations. Solid circles indicate macrophages. The micrographs in Panels C and D indicate results obtained from fluorescent immunostaining with F4/80, a macrophage specific marker, and nuclei-specific marker. Panels A-D are at 400× magnification.
Figure 1B:
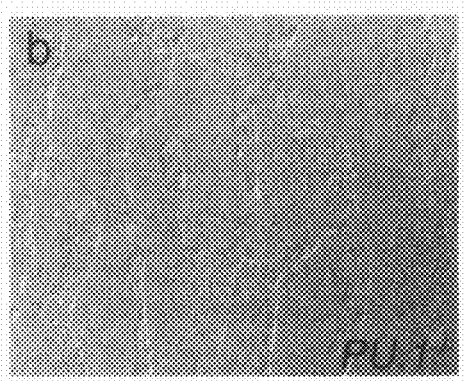
Figure 1C:
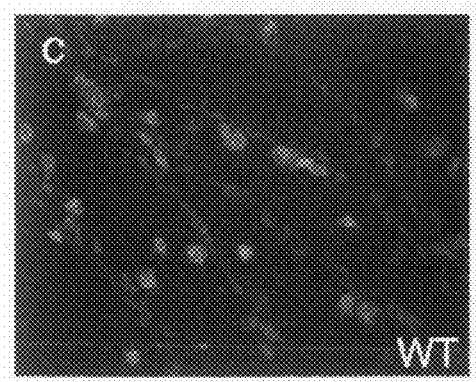
Figure 1D:
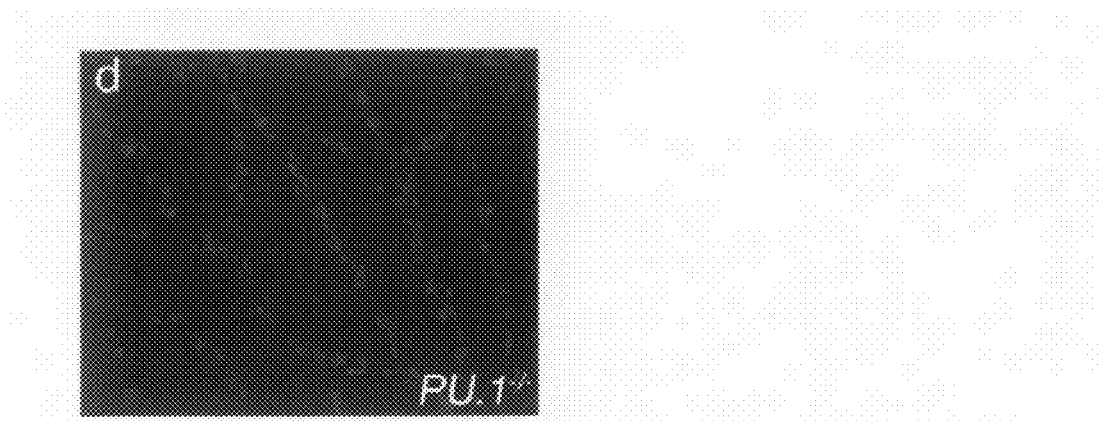
Figure 1E:
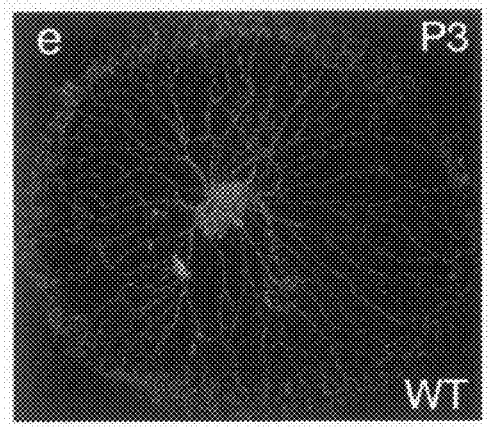
Figure 1F:
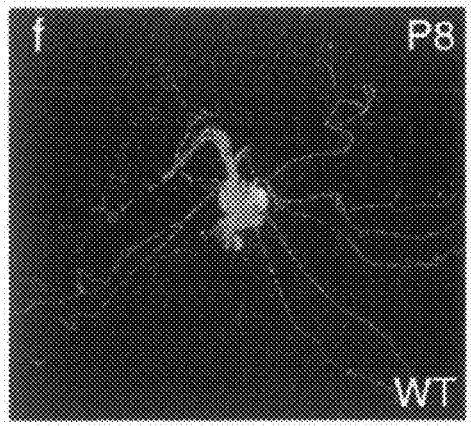
Figure 1G:
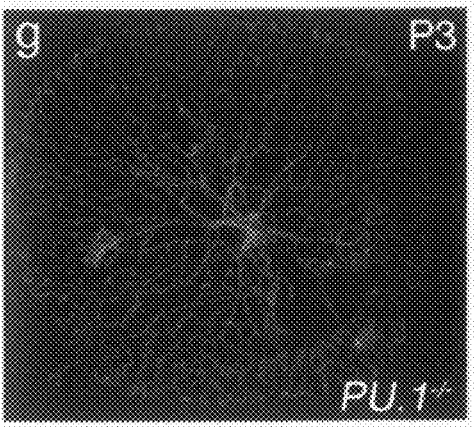
Figure 1H:
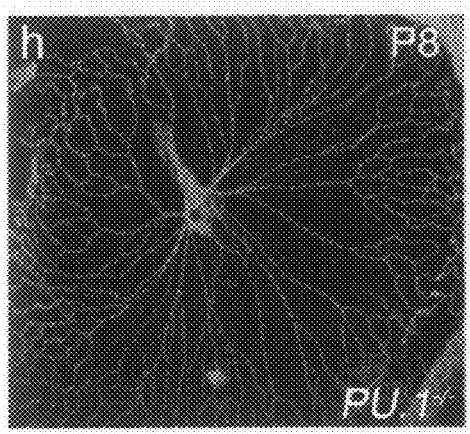
Figure 1I:
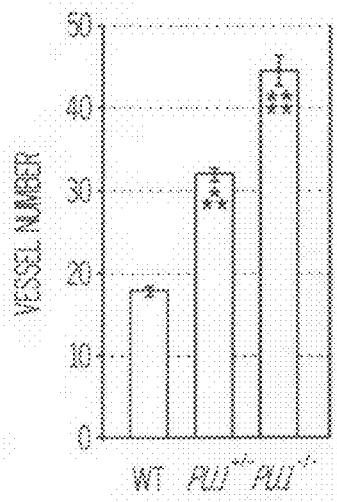
Figure 2A:
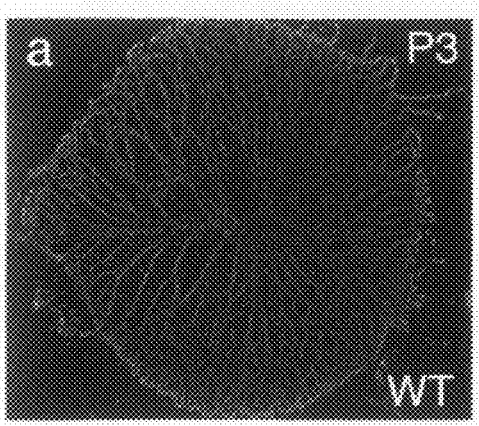
Figure 2B:
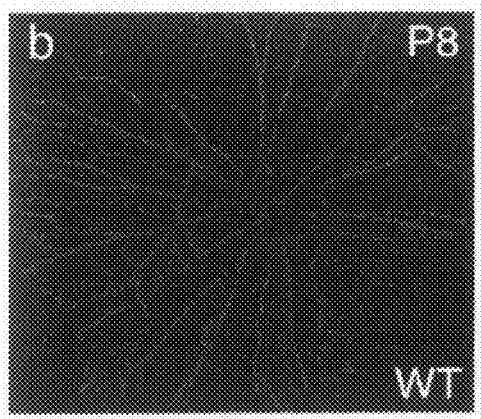
Figure 2C:
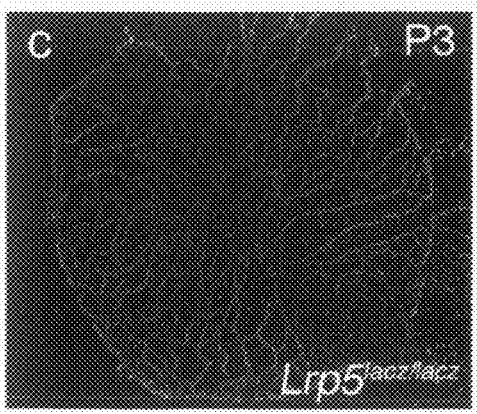
Figure 2D:
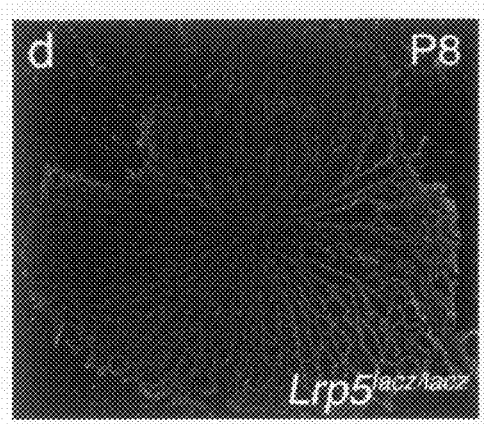
Figure 2E:
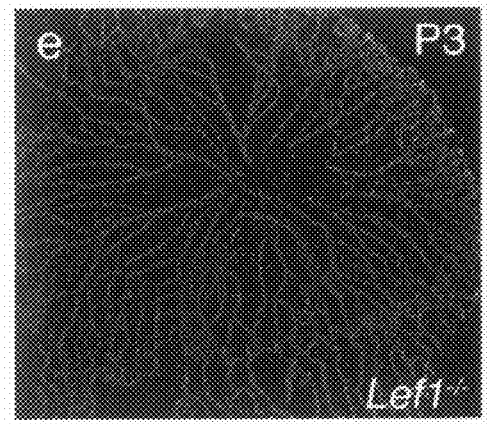
Figure 2F:
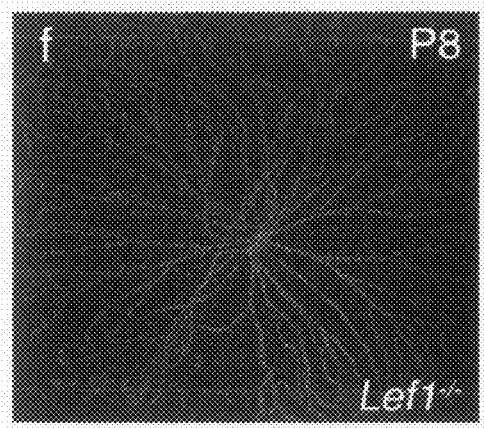
Figure 2G:
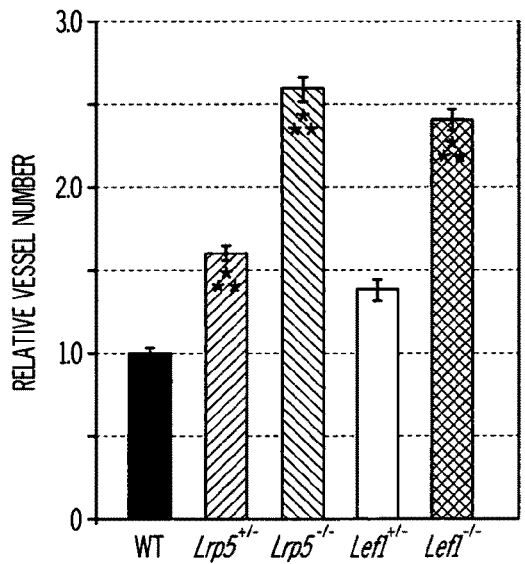
Figure 2H:
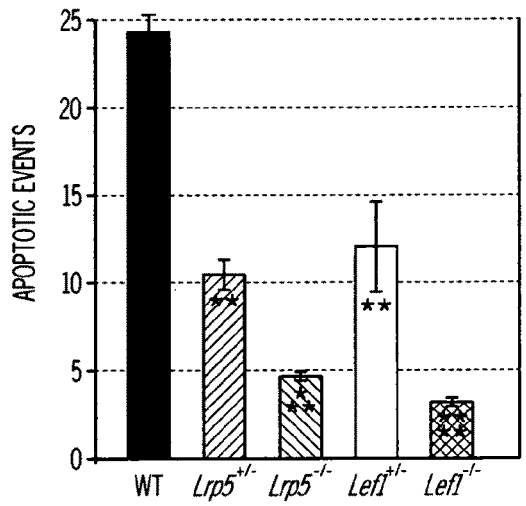
Figure 2I:
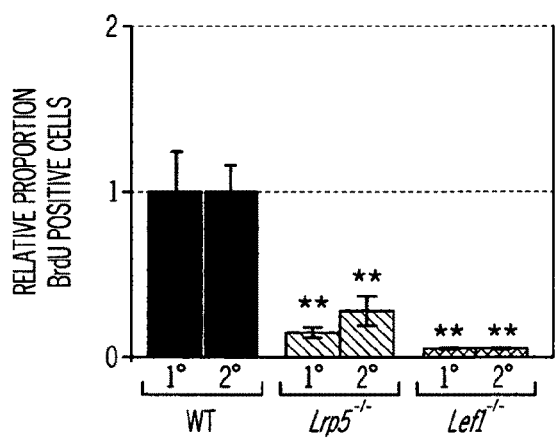
Figure 2J:
Figure 2K:
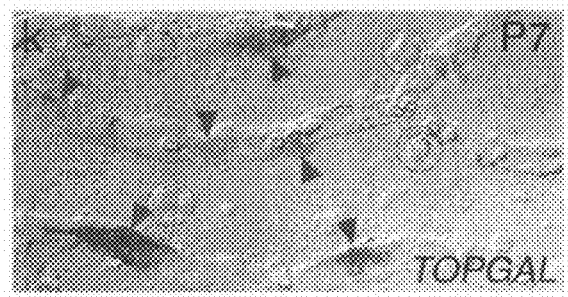
Figure 2L:
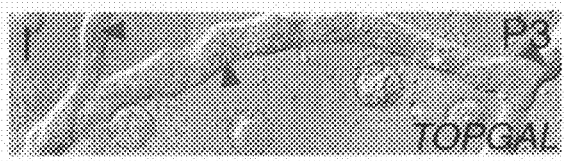
Figure 2M:
Figure 2N:
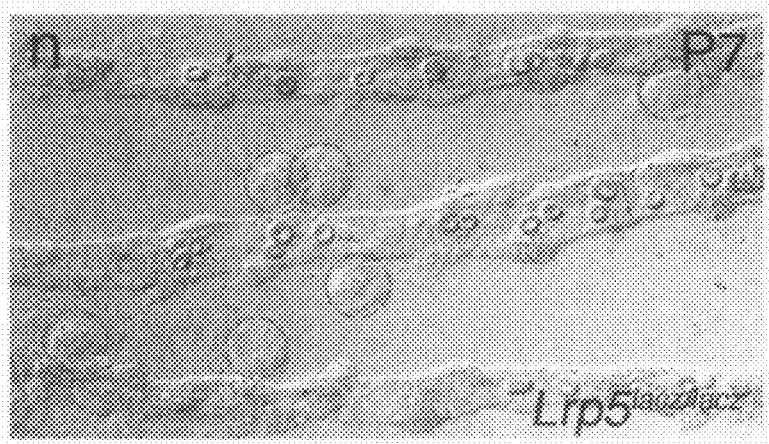
Figure 2O:
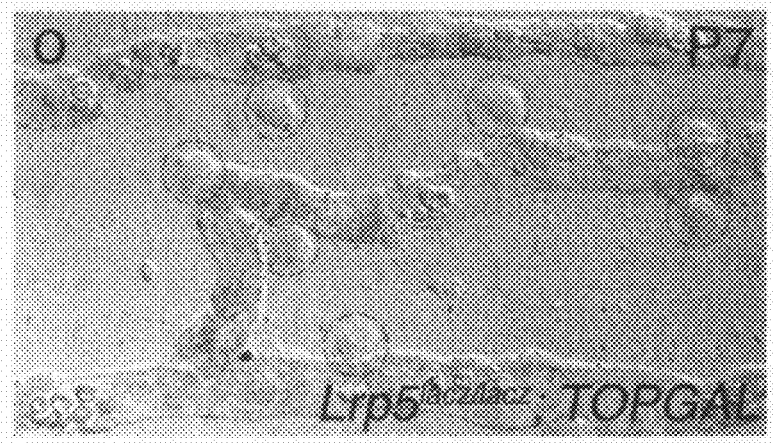

FIG. 2 presents the results of experiments performed to assess the role of the Wnt pathway response in vascular endothelial cells (VEC) and hyaloid vessel regression. Panels A-F present micrographs of Hoechst 33258 stained hyaloid vessel preparations obtained from the indicated mice at a 50× magnification. The vessels in Panels A and B were obtained from wild-type mice at P3 and P8 respectively. The vessels in Panels C and D were obtained from Lrp5$^{lacZ/lacZ}$ mice at P3 and P8 respectively. The vessels in Panels E and F were obtained from Lef1$^{-/-}$ mice at P3 and P8 respectively.

The graphs in panels G-I summarize the relative vessel number (Panel G), the number of apoptotic events (Panel H), and the relative proportion of 5'-bromo-deoxyuridine (BrdU)-Positive cells (Panel I) in five mice strains at the indicated age. Results from wild-type (WT) mice are indicated with solid bars; results from Lrp5$^{+/-}$ mice are indicated with hatched bars; results from Lrp5$^{-/-}$ mice are indicated with counter-hatched bars; results from Lef1$^{+/-}$ mice are indicated with empty bars; and results from Lef1$^{-/-}$ mice are indicated with cross-hatched bars. In Panel I, results obtained from primary and secondary hyaloid capillary branches are indicated separately.

Panels J-O present micrographs of X-gal stained hyaloid vessels from mice of the indicated genotype and age. Panel J is at a 1000× magnification; Panels K-O are at 630× magnification. Intensely stained TOPGAL expressing cells are indicated by arrowheads; resident macrophages are indicated by dashed circles. The vessels in Panels J-M were obtained from TOPGAL mice at P7 (Panels J-K), P3 (Panel L), and P5 (Panel M). The vessels in Panel N were obtained from Lrp5$^{lacZ/lacZ}$ mice at P7. The vessels in Panel O were obtained from Lrp5$^{lacZ/lacZ}$/TOPGAL mice at P7.

Figure 3A:
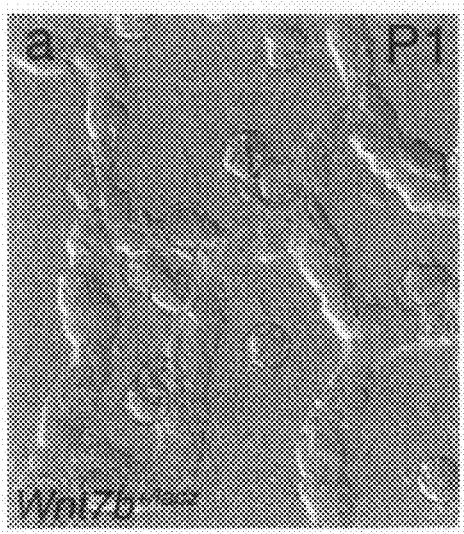
Figure 3B:
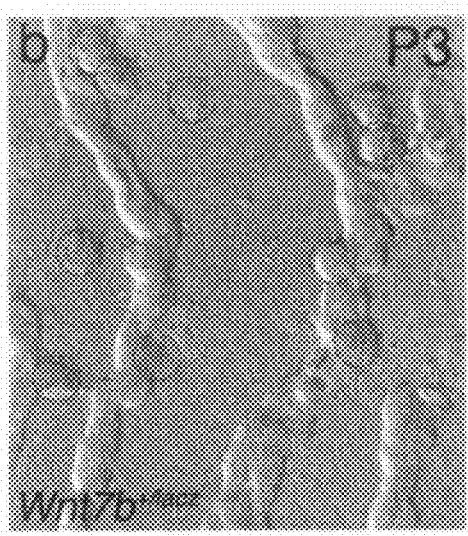
Figure 3C:
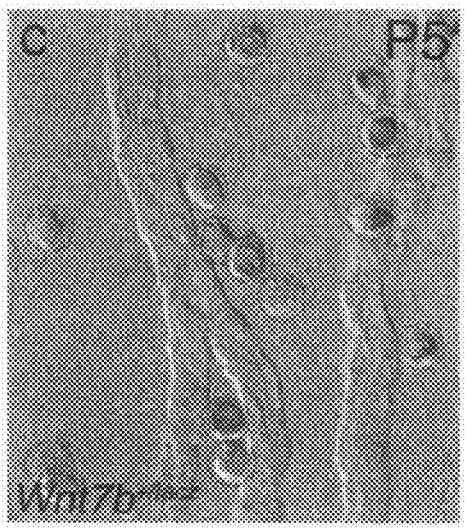
Figure 3D:
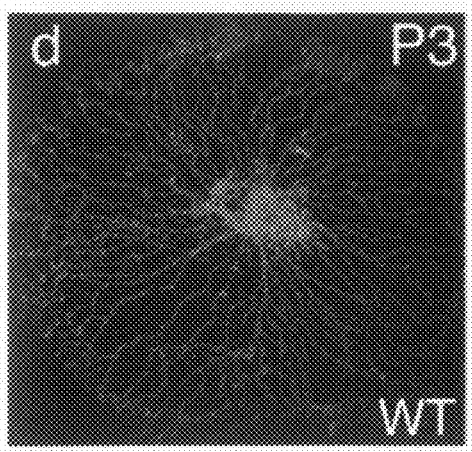
Figure 3E:
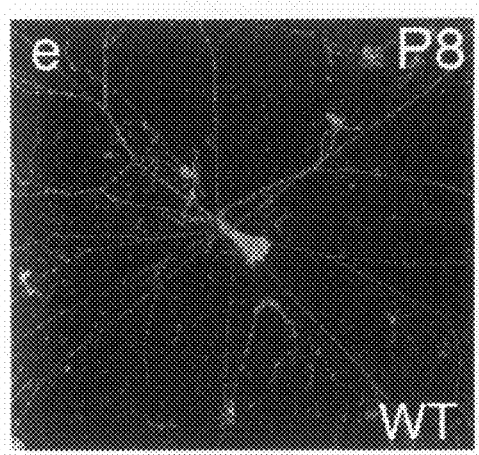
Figure 3F:
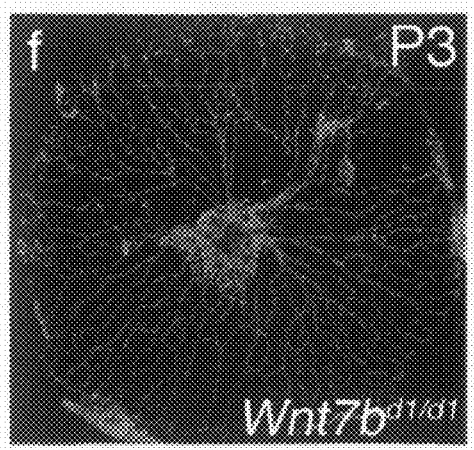
Figure 3G:
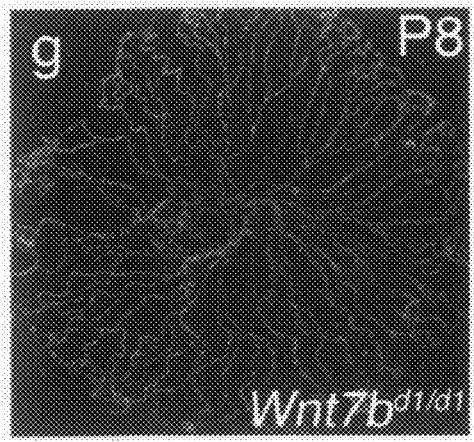
Figure 3I:
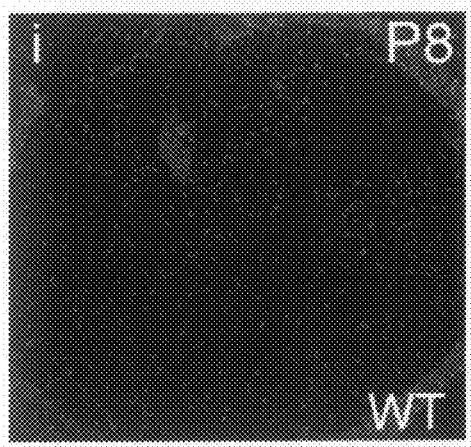
Figure 3J:
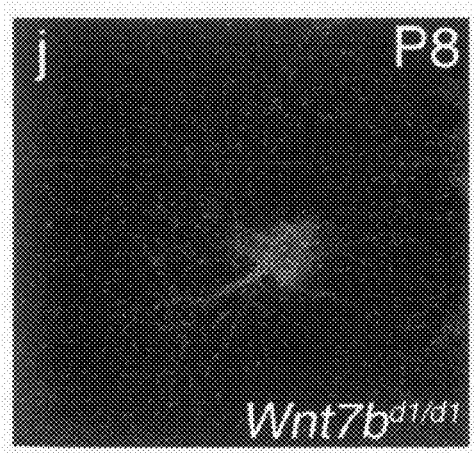
Figure 3H:
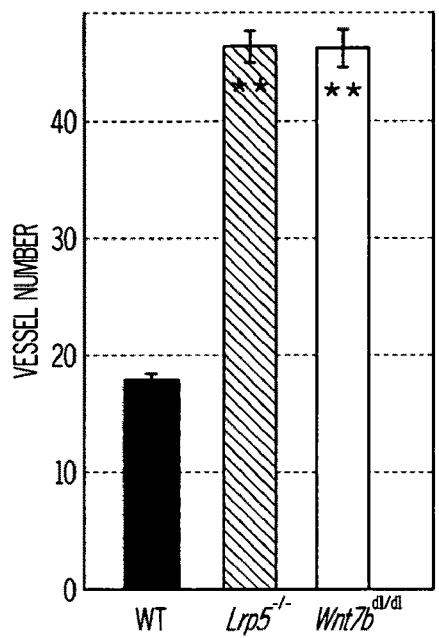
Figure 3K:
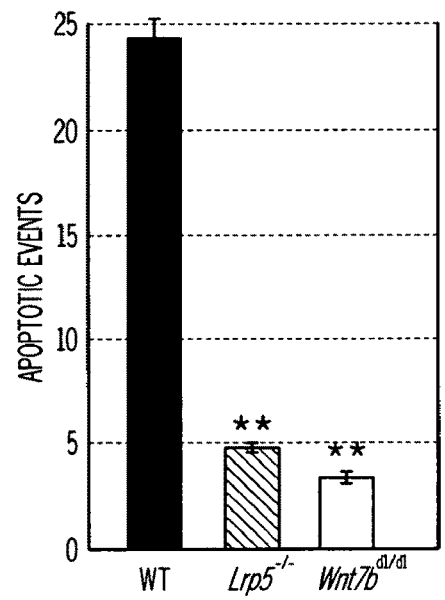
Figure 3L:
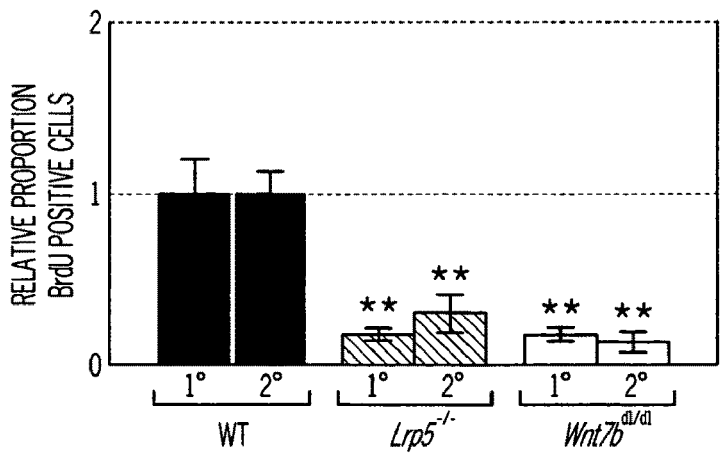

FIG. 3 presents results from experiments investigating Wnt7b expression in macrophages and involvement in hyaloid cell regression. Panels A-C present micrographs (630× magnification) of X-gal stained hyaloid vessels from Wnt7b$^{+/lacZ}$ mice at P1, P3, and P5 respectively. Dashed circles indicate macrophages. Micrographs of vessels from wild-type (WT) mice at the indicated ages are shown in Panels D, E, and I. Micrographs of vessels from Wnt7b$^{d1/d1}$ mice at the indicated ages are shown in Panels F, G, and J. The preparations in Panels D-G were stained with Hoechst 33258. The preparations in Panels I-J were stained with anti-F4/80.

The graphs in Panels H and K-L summarize quantification in hyaloid vessels of the vessel number at P8 (Panel H), apoptotic events at P5 (Panel K), and the relative proportion of BrdU-positive cells at P5 (Panel L). Results from wild-type (WT) mice are indicated with solid bars; results from Lrp5$^{-/-}$ mice are indicated with counter-hatched bars; results from Wnt7b$^{d1/d1}$ mice are indicated with empty bars. In Panel L, results obtained from primary and secondary hyaloid capillary branches are indicated separately.

Figure 4A:
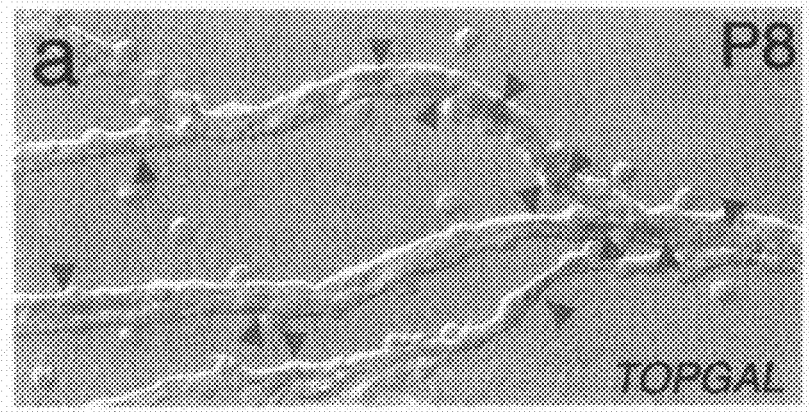
Figure 4B:
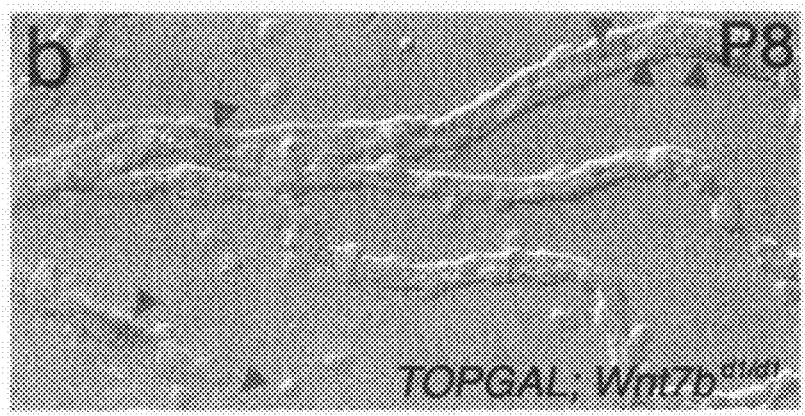
Figure 4C:
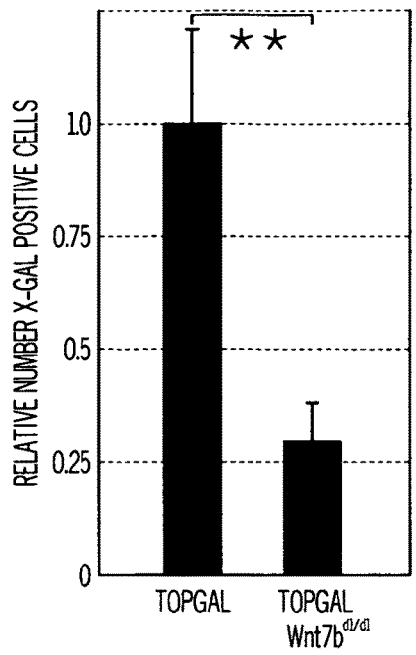
Figure 4D:
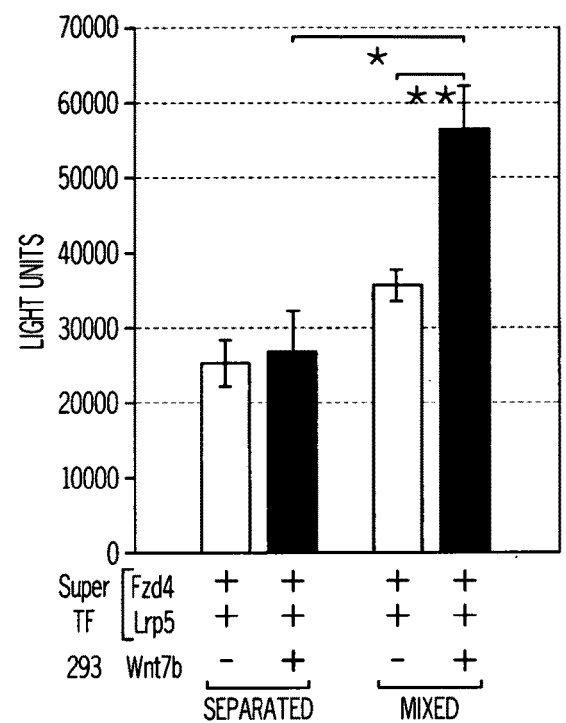
Figure 4E:
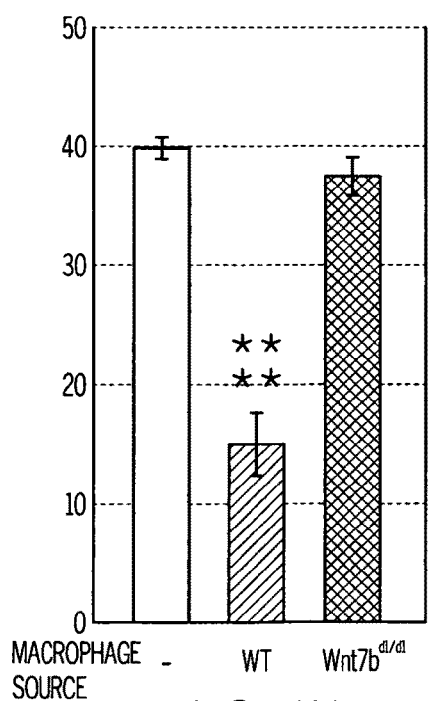
Figure 4F:
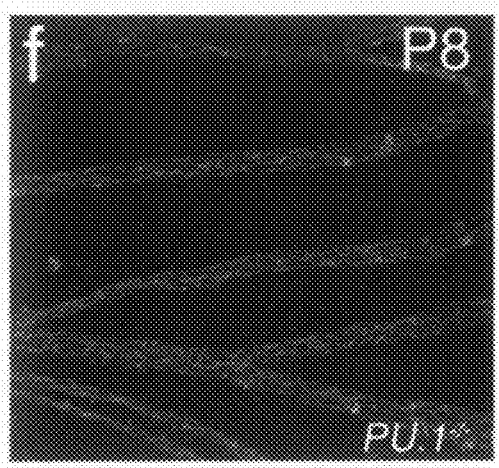
Figure 4G:
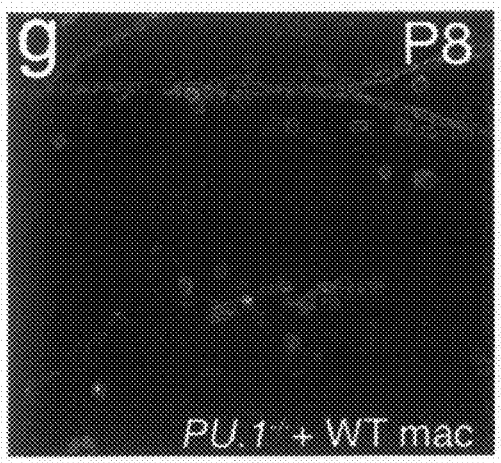
Figure 4H:
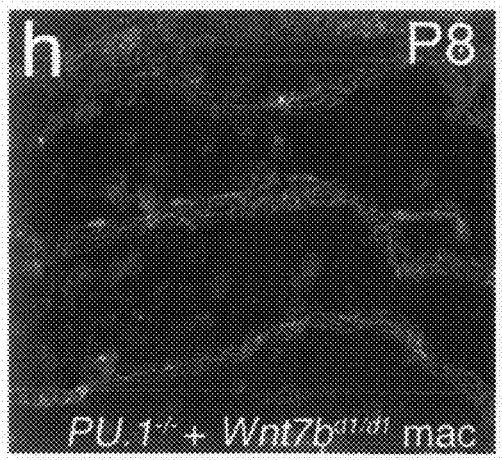

FIG. 4 presents results from experiments investigating Wnt7b expression in macrophages and involvement in hyaloid cell regression. Panels A and B present micrographs of hyaloid vessels stained with X-gal obtained from TOPGAL and TOPGAL/Wnt7b$^{d1/d1}$ mice, respectively. Arrowheads indicate stained cells.

Panel C summarizes the relative number of X-gal stained cells in hyaloid preparations at P8 from TOPGAL (solid bar) and TOPGAL/Wnt7b$^{d1/d1}$ (empty bar) mice. The data are normalized for the increased vessel number of the Wnt7b$^{d1/d1}$ mice.

Panel D summarizes the light units produced by SuperTopFlash cells transfected with Fzd4 and Lrp5 in the presence (+) or absence (−) of Wnt7b producer cells. The data in the left two columns were obtained from experiments performed under conditions which restricted mixing of the two cell types (separated). The data in the right two columns were obtained from experiments performed under conditions which allowed mixing of the two cell types (mixed).

Panels E-G present micrographs of hyaloid vessel preparations stained with F4/80, vascular endothelial cell cadherin, and nuclei. The hyaloid vessel preparations were obtained from PU.1$^{-/-}$ mice either uninjected (Panel E), injected with wild-type macrophages (WT mac, Panel F), or injected with Wnt7b$^{d1/d1}$ derived macrophages (Wnt7b$^{d1/d1}$ mac, Panel G). Panel H presents a graphical summary of the vessel number at P8 in uninjected PU.1$^{-/-}$ (empty bar) mice, PU.1$^{-/-}$ mice injected with wild-type macrophages (hatched bar), or PU.1$^{-/-}$ mice injected with Wnt7b$^{d1/d1}$ derived macrophages (cross-hatched bar). Error bars indicate standard error.

DETAILED DESCRIPTION OF THE INVENTION

The invention provides compositions and methods for modulating vascular endothelial cells, vascular endothelial cell vessels, capillary vessel development, capillary bed development, and angiogenesis. Additionally, the invention provides methods of modulating vascular endothelial cell-related and angiogenic-related disorders. The compositions and methods of the invention were developed from investigations that revealed that Wnt7b and angiopoietin-2 (Ang-2) modulate the regression of vascular endothelial vessels. Prior work in the field suggested that Wnt7b facilitates the early stages of tumorigenesis (U.S. Pat. No. 6,653,448, herein incorporated by reference in its entirety). Prior to this work it was recognized that the Wnt signaling pathway is often a stimulus for proliferation; thus the results of the investigations described herein were unexpected.

Compositions of the invention include a vascular endothelial cell vessel modulating compound. A "vascular endothelial cell vessel modulating compound" of the invention comprises a Wnt pathway stimulator component and a Tie2 pathway repressor component. By "Wnt pathway stimulator" is intended any agonist of the Fzd4 receptor, any Dv1 activator, any GSK3 repressor, any β-catenin modulator, or any Lef1 stimulator that results in increased myc and cyclinD1 expression or results in advancement of the cell through the cell cycle. Wnt pathway stimulators include but are not limited to Wnt7b-like molecules and Wnt7b expression modulating agents.

By "Wnt7b-like molecule" is intended an agent capable of interacting with a Fzd4 receptor. Wnt7b-like molecules include, but are not limited to, an isolated nucleic acid molecule having the nucleotide sequence set forth in SEQ ID NO:1; an isolated nucleic acid molecule having a nucleotide sequence that encodes a polypeptide having the amino acid sequence set forth in SEQ ID NO:2 or SEQ ID NO:3; an isolated nucleic acid molecule having a nucleotide sequence that encodes a polypeptide having at least 95% identity to the amino acid sequence set forth in SEQ ID NO:2 or SEQ ID NO:3; an isolated nucleic acid molecule having a nucleotide sequence having at least 95% identity to the nucleotide sequence set forth in SEQ ID NO:1 wherein said nucleotide sequence encodes a polypeptide capable of interacting with a Fzd4 receptor, such as the Wnt7b nucleotide sequence set forth in SEQ ID NO:4; a polypeptide having an amino acid sequence encoded by a nucleotide sequence set forth in SEQ ID NO:1 or SEQ ID NO:4; a polypeptide having an amino acid sequence set forth in SEQ ID NO:2, SEQ ID NO:3; a polypeptide having 95% identity to an amino acid sequence set forth in SEQ ID NO:2 or SEQ ID NO:3 such as a polypeptide having the amino acid sequence set forth in SEQ ID NO:5 or SEQ ID NO:6; a fragment of an above described polypeptide or nucleotide sequence; or any small molecule, glycoprotein, peptidomimetic, lipid, antibody, ligand, sterol, steroid, hormone, kinase, kinase inhibitor, enzyme, enzyme inhibitor, carbohydrate, deaminase, deaminase inhibitor, G-protein, G-protein receptor inhibitor, calcium channel modulator, hormone receptor modulator, alcohol, phosphatase, or lactone capable of binding the Fzd4 receptor (Genbank NM_012193). Some Wnt7B-like molecules are described in U.S. Pat. No. 6,653,448 B1, herein incorporated by reference in its entirety. Particularly preferred Wnt7b-like molecules include Mus musculus Wnt7b (Genbank Acc. No. BC0066004), the nucleotide sequence of which is set forth in SEQ ID NO:1, the amino acid sequence of which is set forth in SEQ ID NO:2 and SEQ ID NO:3; Homo sapiens Wnt7b (Genbank Acc. No. AB062766), the nucleotide sequence of which is set forth in SEQ ID NO:4, the amino acid sequence of which is set forth in SEQ ID NO:5 and SEQ ID NO:6; and fragments and variants thereof. Methods of assessing receptor binding are known in the art and described elsewhere herein. Any method of assessing expression level known in the art may be used to assess myc or cyclin D expression. Methods of assessing expression levels are described elsewhere herein. Methods of assessing cell cycle stage are known in the art and described elsewhere herein.

By "Tie2 pathway repressor" is intended any Tie2 receptor antagonist including but not limited to, an Ang2-like molecule, or any Bad activator, Casp9 activator, or FH activator. By "Ang2-like molecule" is intended an isolated Ang2 nucleic acid molecule having the nucleotide sequence of set forth in SEQ ID NO:7 or having 95% identity to the nucleotide sequence set forth in SEQ ID NO:7; an isolated Ang2 polypeptide having the amino acid sequence set forth in SEQ ID NO:8 or SEQ ID NO:9 or having 95% identity to the amino acid sequence set forth in SEQ ID NO:8 or SEQ ID NO:9; an isolated Ang2 nucleic acid molecule having the nucleotide sequence of set forth in SEQ ID NO:10 or having 95% identity to the nucleotide sequence set forth in SEQ ID NO:10; an isolated Ang2 polypeptide having the amino acid sequence set forth in SEQ ID NO:11 or SEQ ID NO:12 or having 95% identity to the amino acid sequence set forth in SEQ ID NO:11 or SEQ ID NO:12; a fragment of an isolated Ang2 nucleic acid molecule encoding a polypeptide capable of interacting with an Ang2 receptor such as Tie2; a fragment of an isolated Ang2 polypeptide capable of interacting with an Ang2 receptor such as Tie2; or a small molecule, glycoprotein, peptidomimetic, lipid, antibody, ligand, sterol, steroid, hormone, kinase, kinase inhibitor, enzyme, enzyme inhibitor, carbohydrate, deaminase, deaminase inhibitor, alcohol, phosphatase, or lactone capable of interacting with Tie2 (Genbank No. AB086825). Particularly preferred Ang2-like molecules include Mus musculus Ang2 (Genbank Acc. No. NM007426), the nucleotide sequence of which is set forth in SEQ ID NO:7, the amino acid sequence of which is set forth in SEQ ID NO:8 and SEQ ID NO:9; Homo sapiens Ang2 (Genbank Acc. No. NM001147), the nucleotide sequence of which is set forth in SEQ ID NO:10, the amino acid sequence of which is set forth in SEQ ID NO:11 and SEQ ID NO:12; and fragments and variants thereof.

The invention encompasses isolated or substantially purified nucleic acid or protein compositions. An "isolated" or substantially "purified" nucleic acid molecule, polypeptide, or biologically active portion thereof, is substantially free of other cellular material or culture medium when produced by recombinant techniques or substantially free of chemical precursors or other chemicals when chemically synthesized. Preferably, an "isolated" nucleic acid molecule is free of sequences (preferably polypeptide encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Fragments and variants of the Wnt7b and Ang2 nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence exhibit a Wnt7b or Ang2 activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a Wnt7b or an Ang2 nucleotide sequence that encodes a biologically active portion of a Wnt7b or an Ang2 protein of the invention will encode at least 15, 25, 30, 50, 100, 150, 200, 250, 300, 350 or 353 contiguous amino acids, or up to the total number of amino acids present in a full-length Wnt7b or at least 15, 25, 30, 50, 100, 150, 200, 250, 300, 350, 400, 450, or 496 contiguous amino acids, or up to the total number of amino acids present in a full-length Ang2 protein of the invention. Fragments of a Wnt7b or an Ang2 nucleotide sequence that are useful as hybridization probes or PCR primers generally need not encode a biologically active portion of a Wnt7b or an Ang2 protein. Polypeptide fragments of particular interest include those comprising the receptor binding region of the polypeptide.

Thus, a fragment of a Wnt7b or an Ang2 nucleotide sequence may encode a biologically active portion of a Wnt7b or an Ang2 or it may be a fragment that can be used as a hybridization probe or PCR primer using methods disclosed below. A biologically active portion of a Wnt7b or an Ang2 can be prepared by isolating a portion of one of the Wnt7b or an Ang2 nucleotide sequences of the invention, expressing the encoded portion of the Wnt7b or an Ang2 protein (e.g., by recombinant expression in vitro), and assessing the activity of the encoded portion of the Wnt7b or an Ang2 protein. Nucleic acid molecules that are fragments of a Wnt7b nucleotide sequence comprise at least 16, 20, 50, 75, 100, 150, 200, 250, 300, 347, 350, 400, 450, 500, 550, 600, 650, 700, 800, 900, 1,000, 1,100, 1,200, 1,300, 1400, 1500, 1600, 1700, 1800, 1900, 2000, 2100, 2200, 2300, 2400, 2500, or 2544 nucleotides, or up to the number of nucleotides present in a full-length Wnt7b nucleotide sequence disclosed herein. Nucleic acid molecules that are fragments of an Ang2 nucleotide sequence comprise at least 16, 20, 50, 75, 100, 150, 200, 250, 300, 347, 350, 400, 450, 500, 550, 600, 650, 700, 800, 900, 1,000, 1,100, 1,200, 1,300, 1400, 1500, 1600, 1700, 1800, 1900, 2000, 2100, 2200, 2300, 2400, or 2475 nucleotides, or up to the number of nucleotides present in a full-length Ang2 nucleotide sequence disclosed herein.

By "variants" is intended substantially similar sequences. For nucleotide sequences, conservative variants include those sequences that, because of the degeneracy of the genetic code, encode the amino acid sequence of one of the Wnt7b or Ang2 polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis [but which still encode a Wnt7b or an Ang2 protein of the invention]. Generally, variants of a particular nucleotide sequence of the invention will have at least about 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, a Wnt7b or an Ang2 activity as described herein. Such variants may result from, for example, genetic polymorphism or from human manipulation. Biologically active variants of a native Wnt7b or an Ang2 protein of the invention will have at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue. Biologically active variants of the polypeptide of the invention include Wnt7b polypeptides from other species such as *H. sapiens* (SEQ ID NOS:5 and 6) and Ang2 polypeptides from other species such as *H. sapiens* (SEQ ID NOS:11 and 12). Additional variants are discussed in Davis et al. (2003) *Nature Structural Biology* 10:38-44 and corrigendum p. 146, herein incorporated by reference in its entirety.

The proteins of the invention may be altered in various ways including amino acid substitutions, deletions, truncations, and insertions. Methods for such manipulations are generally known in the art. For example, amino acid sequence variants of the Wnt7b or an Ang2 protein can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired Wnt7b or Ang2 activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by Wnt7b or Ang2 assays such as, but not limited to, receptor binding assays, immunological assays, or secretion assays. See, for example, U.S. Pat. No. 6,653,448; PCT Publication WO 03/004045; Davis et al. (2002) *Nature Structural Biology* 10:44; and Robitaille et al. (2002) *Nature Genetics* 32:326-330; herein incorporated by reference in their entirety.

Variant nucleotide sequences and proteins also encompass sequences and proteins derived from a mutagenic and recombinogenic procedure such as DNA shuffling. With such a procedure, one or more different Wnt7b or Ang2 coding sequences can be manipulated to create a new Wnt7b or Ang2 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Wnt7b or an Ang2 gene of the invention and other known Wnt7b or an Ang2 genes to obtain a new gene coding for a protein with an altered property of interest e.g. receptor binding, agonism, or antagonism. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

(b) As used herein "comparison window" makes reference to a contiguous and specified segment of a polynucleotide sequence, wherein the polynucleotide sequence in the comparison window may comprise additions or deletions (i.e. gaps) compared to the reference sequence (which does not comprise additions or deletions) for optimal alignment of the two sequences. Generally the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Computer implementations of these mathematical algorithms can be utilized for comparison of sequences to determine sequence identity. For purposes of the present invention, comparison of nucleotide or protein sequences for determination of percent sequence identity to the sequences disclosed herein is preferably made using the Multiple Sequence Alignment V2.0: http://xylian.igh.cnrs.fr/msa/msa.html with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially complementary is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Methods of assaying interaction of a compound with an Ang2 receptor such as Tie2 or a Wnt7b receptor such as Fzd4 are known in the art. Any method known in the art for assessing protein-protein interaction such as, but not limited to, SPR, immunoprecipitation, co-immunoprecipitation, receptor binding assays, yeast 2-hybrid, phosphorylation assays, dephosphorylation assays, Western blots, ELISA, cross-linking experiments, chemiluminescence, silver staining, enzymatic assays, ponceau S staining, multiplex RT-PCR, immunohistochemical assays, radioimmunoassay, colorimetric analysis, immunoradiometric assays, immunochemistry, positron emission tomography, Northern blotting, fluorometric assays, fluorescence activated cell sorter staining of permeabilized cells, and radioimmunosorbent assays, is suitable for use in the invention. See for example, Davis et al. (2003) *Nature Structural Biology* 10:38-44; Walker, John, ed. (2002) *Protein Protocols on CD-ROM v. 2*; and Ausubel et al., eds. (1995) *Current Protocols in Molecular Biology*, (Greene Publishing and Wiley-Interscience, New York); WO 03/004045; Robitaille et al. (2002) *Nature* 32:326-330; herein incorporated by reference in their entirety.

A "Wnt7b expression modulating agent" is a compound or agent that results in an altered Wnt7b expression level compared to the Wnt7b mRNA or protein expression level observed in the absence of the compound. Wnt7b expression modulating agents can be identified in a method wherein a cell is contacted with a candidate compound and the expression of Wnt7b mRNA or protein in the cell is determined. The level of expression of Wnt7b mRNA or protein in the presence of the compound is compared to the Wnt7b mRNA or protein expression level in the absence of the candidate compound. The candidate compound can then be identified as a modulator of Wnt-7b expression based on this comparison. For example, when Wnt7b mRNA or protein expression levels are significantly greater in the presence of the compound than its absence, the candidate compound is identified as a stimulator of Wnt7b expression. Alternatively when expression of Wnt7b is significantly less in the absence of the compound than in its presence, the candidate compound is identified as an inhibitor of Wnt7b expression. The level of Wnt7b mRNA or protein expression in the cells can be determined by expression level assays described elsewhere herein. A significant increase in expression level is an increase in the range of 1% to 1000%, particularly 5% to 500%, more particularly 5% to 250%, yet more particularly 10% to 100%. A significant decrease in expression level is a decrease in the range of 1% to 100%, particularly 5% to 100%, more particularly 10% to 100%, yet more particularly 20% to 100%, yet still more particularly 30% to 100%, even yet still more particularly 50% to 100%.

Methods of determining expression levels are known in the art and include, but are not limited to, qualitative Western blot analysis, immunoprecipitation, radiological assays, polypeptide purification, spectrophotometric analysis, Coomassie staining of acrylamide gels, ELISAs, RT-PCR, 2-D gel electrophoresis, microarray analysis, in situ hybridization, chemiluminescence, silver staining, enzymatic assays, ponceau S staining, multiplex RT-PCR, immunohistochemical assays, radioimmunoassay, colorimetric analysis, immunoradiometric assays, positron emission tomography, Northern blotting, fluorometric assays and SAGE. See, for example, Ausubel et al, eds. (2002) Current Protocols in Molecular Biology, Wiley-Interscience, New York, N.Y.; Coligan et al (2002) Current Protocols in Protein Science, Wiley-Interscience, New York, N.Y.; and Sun et al. (2001) *Gene Ther.* 8:1572-1579, herein incorporated by reference.

Methods of determining cell cycle stage are known in the art and include, but are not limited to, flow cytometry, centrifugal elutriation, immunofluorescence, BrdU incorporation, cyclin dependent kinase activity assays, propidium iodide staining, DAPI staining, Hoechst 33342 staining, cyclin D expression analysis, cyclin E expression analysis, cyclin A expression analysis, cyclin B1 expression analysis, tritiated thymidine incorporation, and counterflow centrifugal elutriation (*Current Protocols in Cell Biology* (2003) John Wiley & Sons; herein incorporated by reference in its entirety).

By "angiogenesis" is intended the process of vascularization of a tissue involving the development of capillary blood vessels or vascular endothelial cell vessels. The process of angiogenesis encompasses the metabolically controlled regression of capillary blood vessels. Examples of naturally occurring metabolically controlled regression of capillary blood vessels include, but are not limited to, regression during ocular development and regression after a local immune or inflammatory response. By "vascular endothelial cell vessel" is intended any vessel or tube comprised primarily of vascular endothelial cells, often also comprised of additional components such as a basal lamina. Vascular endothelial cell vessels include those formed in vivo or in vitro. The length, diameter, and continuity of a vascular endothelial cell vessel ranges. See Frietas Jr., R. A. (1999) *Nanomedicine, Volume I: Basic Capabilities* Landes Bioscience Georgetown Tex. and Gray, Henry. *Anatomy of the Human Body*. Philadelphia: Lea & Febiger, 1918; Bartleby.com, 2000. www.bartleby.com/107/. Sep. 8, 2005, Section V Angiology; herein incorporated by reference in their entirety. By "vascular endothelial cell" is intended a simple squamous epithelial cell such as those comprising the simple squamous epithelial tissue lining the blood vessels.

By "angiogenic-related disorder" is intended any disorder, disease, or developmental condition that involves atypical growth, extension, retention, development, progression, increase, or persistence of a blood vessel such as, but not limited to, a capillary blood vessel, wherein the majority of cells in said blood vessel are vascular endothelial cells. Angiogenic related disorders include, but are not limited to, angiomas, capillary angiomas, hemangioma, capillary angioma, angioma simplex, angioma cavernosum, cherry angioma, senile angioma, serpigninous angioma, spider angioma, telangiectactic angioma, angioma venosum racemosum, angiomalacia, angiomatosis, angiomegaly, angiomyoma, angiomyosarcoma, angiomyoneuroma, angiosarcoma, angioscotoma, angiosis, angiotelectasis, angiotitis, vasculitis, Wegener's granulomatosis, Henoch-Schönlein purpura, microscopic polyangiitis, hemangioma, hypersensitivity vasculitis, erythema nodosum, arteriovenous fistulas, damage response, irritant response, ocular angiogenic disorders, hypoxia response, vascular tumor, and hyperproliferative disorders such as, but not limited to, vascularized tumors, cancers, and neoplasms.

By "vascular endothelial cell vessel-related disorder" is intended any disorder or disease involving a tissue comprising a vascular endothelial cell vessel wherein the tissue exhibits a disorder; of particular interest are developmental disorders and hyperproliferative disorders.

The terms "cancer" or "neoplasms" include malignancies of the various organ systems, such as those affecting the lung, breast, thyroid, lymphoid, gastrointestinal, or genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Tumors and cancers of the blood vessels include, but are not limited to hemangioma, lymphangioma, glomus tumor (glomangioma), vascular ectasias, and bacillary angiomatosis, and intermediate-grade (borderline low-grade malignant) tumors, such as Kaposi sarcoma and hemangioendothelioma, and malignant tumors, such as angiosarcoma and hemangiopericytoma.

Tumors and cancers of the skin include, but are not limited to, malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis.

Tumors and cancers of cells found in the bone marrow include, but are not limited to, disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including Kaposi's sarcoma; fibroadenoma and phyllodes tumors, including mammary fibroadenoma; stromal tumors; phyllodes tumors, including histiocytoma; T-cell lymphomas; and B-cell lymphomas.

Tumors and cancers of the heart include, but are not limited to, primary cardiac tumors, such as myxoma, lipoma, papillary fibroelastoma, rhabdomyoma, and sarcoma, and cardiac effects of noncardiac neoplasms.

Tumors and cancers of the B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

Tumors and cancers of the liver include, but are not limited to nodular hyperplasias, adenomas, and malignant tumors, including primary carcinoma of the liver and metastatic tumors.

Tumors and cancers of the brain include, but are not limited to gliomas, including astrocytoma, including fibrillary (diffuse) astrocytoma and glioblastoma multiforme, pilocystic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromatosis, including Type 1 neurofibromatosis (NF1) and TYPE 2 neurofibromatosis (NF2), tuberous sclerosis, and Von Hippel-Lindau disease.

Tumors and cancers of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Tumors and cancers of the kidney include, but are not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Tumors and cancers of the skeletal muscle include, but are not limited to, rhabdomyosarcoma.

Tumors and cancers of the bone-forming cells include, but are not limited to, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Tumors and cancers of the pancreas include, but are not limited to, cystic tumors and carcinoma of the pancreas; islet cell tumors, including but not limited to, insulinomas, gastrinomas, and other rare islet cell tumors.

Tumors and cancers of the breast include, but are not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Tumors and cancers of the male breast include, but are not limited to, carcinoma.

Tumors and cancers of the prostate include, but are not limited to, carcinoma.

Tumors and cancers of the colon include, but are not limited to, non-neoplastic polyps, adenomas, familial syndromes, colorectal carcinogenesis, colorectal carcinoma, and carcinoid tumors.

Tumors and cancers of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pleural tumors, including solitary fibrous tumors (pleural fibroma) and malignant mesothelioma.

Tumors and cancers of the thymus include, but are not limited to, thymomas, including germ cell tumors, lymphomas, Hodgkin disease, and carcinoids. Thymomas can include benign or encapsulated thymoma, and malignant thymoma Type I (invasive thymoma) or Type II, designated thymic carcinoma.

Tumors and cancers of the tonsils include, but are not limited to, non-Hodgkin's lymphoma and B-cell lymphoma.

The invention provides compositions with a vascular endothelial cell modulating activity and methods of modulating angiogenesis, angiogenic-related disorders, a vascular endothelial cell vessel, vascular endothelial cell vessel-related disorders, capillary bed development, and apoptosis of a vascular endothelial cell. By "modulating" is intended a change of at least 1%, 5%, preferably 10%, 20%, more preferably 30%, 40%, 50%, 60%, 70%, 80%, 90%, 99% or more in the volume or number of vascular endothelial cells in a target area or a change in the cell cycle stage of a vascular endothelial cell. Modulation of vascular endothelial cell vessels may be evaluated by any means known in the art including but not limited to those methods described elsewhere herein. In an embodiment a vascular endothelial cell modulating composition of the invention causes a vascular endothelial cell vessel to regress, diminish, shrink, retreat, disappear, reverse, leave, depart, retract, or decrease. Such a regression may result from apoptosis of one or more vascular endothelial cells constituting the vascular endothelial cell vessel of interest.

By "apoptosis" or "programmed cell death" is intended a normal physiological process requiring regulated metabolic activity by the dying cell often characterized by fragmentation of the genomic DNA or other physiological alterations. Physiological alterations of the cell associated with apoptosis include, but are not limited to, DNA fragmentation, MC540 incorporation, annexin V-FITC binding, propidium iodide (PI) labeling of hypodiploid nuclei, lactate dehydrogenase (LDH) release, caspase-3 activation, presence of cyclin D1, cytochrome c leakage from the mitochondria, BAX cellular redistribution, cleavage of poly (ADP-ribose) polymerase (PARP) to an 85-kDa apoptotic fragment, dissipation of the mitochondrial transmembrane potential, phosphatidylserine exposure, tissue transglutaminase activation, cell shrinkage, chromatin condensation, nuclear fragmentation, loss of membrane integrity, blebbing of plasma membranes, loss of membrane integrity, or cell membrane permeability to PI. Apoptosis can be assessed by any method of assessing an apoptotic characteristic known in the art such as, but not limited to, a colorimetric assay, propidium iodide labeling, flow cytometry, TUNEL, ISEL, rhodamine 123 fluorescence, $DIOC_6(3)$ fluorescence, immunocytochemical detection by Zenon technology, FLICAs, PARP cleavage assays, detergent resistance assays, and cadaverine binding (*Current Protocols in Cell Biology* (2003) John Wiley & Sons; herein incorporated by reference in its entirety).

An agent of the invention comprising a Wnt pathway stimulator and a Tie2 pathway repressor (also referred to herein as "active compounds") can be incorporated into pharmaceutical compositions suitable for administration to a subject. Such compositions typically comprise a Wnt pathway stimulator and a Tie2 pathway repressor, and a pharmaceutically acceptable carrier.

By "subject" is intended a mammal, e.g., a human, or an experimental or animal or disease model or mammalian tissue or mammalian cells. Suitable subjects include mammals, particularly humans, at risk for an angiogenic-related disorder, particularly a vascular endothelial cell related disorder; mammals, particularly humans, exhibiting an angiogenic-related disorder, such as but not limited to a vascular endothelial cell related disorder; tissue obtained from a mammal exhibiting an angiogenic-related disorder; cells obtained from a mammal exhibiting an angiogenic-related disorder; cells cultured from a mammal exhibiting an angiogenic-related disorder; and mammals, particularly humans, at risk for a vascular endothelial cell vessel related disorder. The subject can also be a non-human mammal such as, but not limited to, a horse, hamster, guinea pig, mouse, rabbit, dog, pig, goat, cow, rat, monkey, chimpanzee, sheep, or other domestic animal. Subjects exhibiting an angiogenic-related disorder can be identified by any means known in the art including, but not limited to, physical examination, visual observation, angiogram, familial history analysis, ultrasound, MRI, bone density scan, and retinal scan.

The term "administer" is used in its broadest sense and includes any method of introducing the compositions of the present invention into a subject. By "subject" is intended a mammal, e.g., a human, or an experimental or animal or disease model. The subject can also be a non-human animal such as, but not limited to, a non-human primate, horse, cow, goat, pig, rabbit, mouse, guinea pig, dog, or other domestic animal. Additionally the compositions of the invention find use in the treatment of disorders described herein. Thus, therapies for angiogenic related disorders or disorders with associated capillary bed development are encompassed herein. "Treatment" is herein defined as the application or administration of an agent of the invention to a patient, or application or administration of an agent of the invention to an isolated tissue or cell line from a patient, who has a disease or symptom of a disease, with the purpose to cure, heal, alleviate, relieve, alter, remedy, ameliorate, improve, or affect the disease or symptoms of the disease.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compounds (e.g., a Wnt pathway activator component and a Tie2 pathway repressor component) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 0.1 µg/kg to about 1500 mg/kg of an agent of the invention is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

The vascular endothelial cell modulating compounds described herein can be administered transdermally. Transdermal administration typically involves the delivery of a pharmaceutical agent for percutaneous passage of the drug into the systemic circulation of the subject or patient. The skin sites include anatomic regions for transdermally administering the drug and include the forearm, abdomen, chest, back, buttock, mastoidal area, and the like.

Other items may be contained in the device, such as other pharmaceutically acceptable carriers, depending on the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, and antipruritic agents.

Another aspect of this invention provides for the topical delivery of an agent of the invention. This treatment regimen is suitable either for the systemic administration of the agent or for localized therapy, i.e., directly to pathological or diseased tissue.

Typically, the topical formulations will comprise a preparation for delivering the agent directly to the affected area comprising the complex, typically in concentrations in the range of from about 0.001% to 10%; preferably, from about 0.01 to about 10%; more preferably from about 0.1 to about 5%; and most preferably from about 1 to about 5%, together with a non-toxic, pharmaceutically acceptable topical carrier (Barry (eds). *Dermatological Formulations: Percutaneous Absorption* (1983) Marcel Dekker, Inc; for standard dosages of conventional pharmaceutical agents see, e.g., Physicians Desk Reference (1992 Edition); and American Medical Association (1992) Drug Evaluations Subscriptions).

Topical preparations can be prepared by combining the agent with conventional pharmaceutical diluents and carriers commonly used in topical dry, liquid, cream, and aerosol formulations. Ointment and creams may, for example, be formulated with an aqueous or oily base with the addition of suitable thickening and/or gelling substances. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, wool fat, hydrogenated lanolin, beeswax, and the like. Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable base, e.g., talc, lactose, starch, and the like. Drops may be formulated with an aqueous base or non-aqueous base also comprising one or more dispersing agents, suspending agents, solubilizing agents, and the like.

Dosage forms for the topical administration of an agent of this invention include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required.

The ointments, pastes, creams, and gels also may contain excipients, such as animal and vegetable fats, oils, waxes, paraffins, starch, tragacanth, cellulose derivatives, polyethylene glycols, silicones, bentonites, talc, and zinc oxide, or mixtures thereof. Powders and sprays also can contain excipients such as lactose, talc, aluminum hydroxide, calcium silicates, and polyamide powder, or mixtures of those substances. Sprays can additionally contain customary propellants, such as chlorofluorohydrocarbons and volatile unsubstituted hydrocarbons such as butane and propane.

The methods of the present invention are also applicable to the delivery of pharmaceutical agents through mucosal membranes such as a gastrointestinal, sublingual, buccal, nasal, pulmonary, vaginal, corneal, and ocular membranes (Mackay et al. (1991) *Adv. Drug Del. Rev.* 7:313-338).

For delivery to the buccal or sublingual membranes, typically an oral formulation such as a lozenge, tablet, or capsule will be used. The method of manufacture of these formulations are known in the art, including, but not limited to, the addition of the agent to a pre-manufactured tablet; cold compression of an inert filler, a binder, and encapsulation.

Another oral formulation is one that can be applied with an adhesive such as the cellulose derivative, hydroxypropyl cellulose, to the oral mucosa, for example as described in U.S. Pat. No. 4,940,587, incorporated by reference. This buccal adhesive formulation, when applied to the buccal mucosa, allows for the controlled release of an agent into the mouth and through the buccal mucosa.

For delivery to the nasal and/or pulmonary membranes, typically an aerosol formulation will be employed. The term "aerosol" includes any gas-borne suspended phase of an agent of the invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of the agent suspended in air or other carrier gas, which may be delivered by inhalation from an inhaler device.

The compositions of the invention are useful to treat any of the disorders discussed herein. The compositions are provided in therapeutically effective amounts. By "therapeutically effective amounts" is intended an amount sufficient to modulate the desired response.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In a preferred example, a subject is treated with a therapeutically effective amount of the agent one time per week for between about 1 to 10 weeks, preferably between 2 to 8 weeks, more preferably between about 3 to 7 weeks, and even more preferably for about 4, 5, or 6 weeks. It will also be appreciated that the effective dosage used for treatment may increase or decrease over the course of a particular treatment. Changes in dosage may result and become apparent from the results of diagnostic assays as described herein.

Where a subject undergoing therapy exhibits a partial response or a relapse following a prolonged period of remission, subsequent course of treatment with an agent of the invention may be administered. Thus, subsequent to a period of time off from a first treatment period, which may have comprised a single dosing regimen or a multiple dosing regimen, a subject may receive one or more additional treatment periods comprising single or multiple dosing regimens. Such a period of time off between treatment periods is referred to herein as a time period of discontinuance. It recognized that the length of the time period of discontinuance is dependent upon the degree of disorder response achieved with any prior treatment periods with the vascular endothelial cell modulating compounds of the invention.

The pharmaceutical compositions can be included in a container, pack, or dispenser together with instructions for administration.

The results of treatment of a disorder may be assayed by any method known to one skilled in the art including, but not limited to, physical examination, laboratory, nuclear, and radiographic studies (i.e. computer tomography and/or magnetic resonance imagery), angiogram, angiography, ultrasound and other procedures.

In an embodiment, the invention provides a compound suitable for use as a cosmetic agent. A cosmetic agent of the invention may further comprise a delivery component such as an ointment or a lotion. A cosmetic agent of the invention finds use in the modulation, reduction, or diminishment of skin lesions characterized by visible capillary bed development or capillary bed persistence. Administration of a cosmetic agent of the invention occurs at a frequency that ranges from hourly to once per decade, particularly daily to annually, more particularly daily to weekly. Administration of a cosmetic agent of the invention may occur on a single occasion or on multiple occasions.

The following examples are offered by way of illustration and not limitation.

EXPERIMENTAL

Example 1

Mouse Breeding and Genotyping

Genotyping of $Lrp5^{lacZ/lacZ}$, $Lef1^{-/-}$, $PU.1^{-/-}$, and TOP-GAL mice was performed as previously described. When Lef1-mutant mice were produced as C57BL6/129 Sv F1 hybrids, they showed enhanced survival that allowed the analysis of hyaloid vessel regression postnatally. See McKercher et al (1996) *EMBO J.* 15:5647-5658; Kato et al. (2002) *J. Cell Biol.* 157:303-314; van Genderen et al. (1994) *Genes Dev.* 8:2691-2703; and DasGupta & Fuchs (1999) *Development* 126:4557-4568, herein incorporated by reference in their entirety.

Example 2

Dissections, Immunostaining, and Imaging

Hyaloid vessel preparation was performed as previously described with the exception that 5% (w/v) gelatin was used at 56° C. and allowed to set on ice before completion of the dissection. X-gal staining was done according to standard protocols. Indirect immunofluorescent staining and BrdU labeling was performed as previously described. Primary antibodies used were anti-vascular endothelial cell cadherin (Santa Cruz), anti-BrdU (Dako), and anti-F4/80 (Caltag Laboratories), all at 1:100 dilution. Secondary antibodies labeled with Alexa fluorochromes (Molecular Probes) were used at a 1:500 dilution. TUNEL labeling of apoptotic cells was performed using an in situ cell death detection kit (Roche).

Example 3

Plasmids

All Wnt complementary DNAs used were mouse. Wnt7b was expressed from pCDNA3 as a V5 and His-epitope tagged fusion protein. In addition, $Fzd4^{m1}$ the sequence encoding the cysteine-rich domain (residues 54-QNLGYNV-60) was modified to encode AALAYAA. In $Fzd4^{m2}$ the sequence encoding 105-MCT-107 was modified to encode ACA. The sequence alterations were made using a PCR-based mutagenesis strategy. The $Fzd4^{m1}$ and $Fzd4^{m2}$ were generated in pCDNA3. These expression plasmids were used in the paracrine and range-of-action signaling assays.

Example 4

Laser Capture Microdissections

Hyaloid macrophages were isolated from whole-mount hyaloid vessel preparations using the PixCell II laser-capture microdissection system (Arcturus). Macrophages were lifted from preparation on the laser-melted polymer membrane.

Example 5

Macrophage Rescue

Mouse bone marrow macrophages were isolated as previously described (Diez-Roux & Lang (1997) *Development* 124:3633-3638, herein incorporated by reference. Approximately 4000 macrophages from wild-type or $Wnt7b^{d1/d1}$ animals were injected into the vitreous at P1 in a volume of 200 nl using a modification of a previously described trans-corneal technique. Animals were sacrificed at P8 and hyaloid vessels dissected.

Example 6

Luciferase and Range of Action Assays

For the Frizzled receptor activity screen SuperTOPFLASH cells carrying a reporter plasmid with Lef/Tcf binding sites and a minimal promoter upstream of an open reading frame encoding luciferase were plated into 60 mM dishes. The cells were transfected after 24 hours with combinations of 1 μg Lrp5-FLAG, 1 μg Wnt7b-V5His, and 0.1 μg Fzd plasmid made up to 4 μg with pIRES-GFP using Fugene 6 (Roche).

Forty-eight hours after transfection, cells were washed with PBS and luciferase activity was measured with a luciferase assay kit (Promega).

For the mixed cell paracrine signaling assay, 293 cells were transfected with plasmids expressing Wnt pathway ligands and overlaid on SuperTOPFLASH responder cells that were separately transfected with plasmids carrying LRP5 and a FZD4 receptor.

Wnt7b range of action experiments were carried out as described in Xu et al. (2004) *Cell* 116:883-895, herein incorporated by reference.

Example 8

Statistical Analysis

Vessel number was quantified using established methods (Huelskin and Birchmeier (2001) *Curr. Opin. Genet. Dev.* 11:547-553, herein incorporated by reference in its entirety). At least four hyaloid vessel preparations were quantified for each experiment. The student's T-test and ANOVA was used to assess statistical significance.

All publications, patents, and patent applications mentioned in the specification are indicative of the level of those skilled in the art to which this invention pertains. All publications, patents, and patent applications are herein incorporated by reference to the same extent as if each individual publication or patent application were specifically and individually incorporated by reference.

Having described the invention with reference to the exemplary embodiments, it is to be understood that it is not intended that any limitations or elements describing the exemplary embodiment set forth herein are to be incorporated into the meanings of the patent claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not be explicitly discussed herein.

Although the foregoing invention has been described in some detail by way of illustration and example for purposes of clarity of understanding, it will be obvious that certain changes and modifications may be practiced within the scope of the appended claims.

That which is claimed:

1. A vascular endothelial cell vessel modulating compound comprising a Wnt pathway stimulator and a Tie2 pathway repressor.

2. The compound of claim 1, wherein the Wnt pathway stimulator is a Wnt7b-like molecule.

3. The compound of claim 2, wherein said Wnt7b-like molecule is a Wnt7b molecule selected from the group consisting of:
   (a) an isolated polypeptide having an amino acid sequence set forth in SEQ ID NO:2, SEQ ID NO:3, SEQ ID:5, or SEQ ID NO:6; and
   (b) an isolated polypeptide having an amino acid sequence having at least 95% identity to an amino acid sequence set forth in SEQ ID NO:2, SEQ ID NO:3, SEQ ID:5, or SEQ ID NO:6, wherein said polypeptide is capable of interacting with a Fzd4 receptor.

4. The compound of claim 1, wherein the Tie2 pathway repressor is an Ang2-like molecule.

5. The compound of claim 4, wherein said Ang2-1 like molecule is an Ang2 molecule selected from the group consisting of:
   (a) an isolated polypeptide having an amino acid sequence set forth in SEQ ID NO:8, SEQ ID NO:9, SEQ ID:11, or SEQ ID NO:12; and
   (b) an isolated polypeptide having an amino acid sequence having at least 95% identity to an amino acid sequence set forth in SEQ ID NO:8, SEQ ID NO:9, SEQ ID:11, or SEQ ID NO: 12, wherein said polypeptide is capable of interacting with Tie2.

6. The compound of claim 1, wherein the Wnt pathway stimulator is a Wnt7b-like molecule and wherein the Tie2 pathway repressor is an Ang2-1 like molecule.

7. A vascular endothelial cell vessel modulating compound comprising a Wnt pathway stimulator and a Tie2 pathway repressor, wherein said Wnt pathway stimulator is a Wnt7b-like molecule and wherein the Tie2 pathway repressor is an Ang2-like molecule.

8. A method of regressing angiogenesis in a subject in need thereof, said method comprising the step of administering to the subject a compound of claim 1, wherein angiogenesis regresses.

9. A method of regressing a vascular endothelial cell vessel in a subject in need thereof, said method comprising the step of administering a compound of claim 1, wherein said vascular endothelial cell vessel regresses.

10. A method of regressing angiogenesis in a subject in need thereof, said method comprising the step of administering to the subject a compound of claim 7, wherein said angiogenesis regresses.

11. The method of claim 10 further comprising the step of evaluating the regression of a vascular endothelial cell vessel subsequent to the administration of said compound.

12. A method of producing apoptosis of a vascular endothelial cell in a subject in need thereof, said method comprising the step of administering to the subject a compound of claim 7, wherein said vascular endothelial cell undergoes apoptosis.

13. A method of regressing a vascular endothelial cell vessel in a subject in need thereof, said method comprising the step of administering a vascular endothelial cell vessel modulating compound comprising a Wnt pathway stimulator and a Tie2 pathway repressor, wherein said Wnt pathway stimulator is a Wnt7b-like molecule and wherein the Tie2 pathway repressor is an Ang2-like molecule, wherein said vascular endothelial cell vessel regresses.

14. The method of claim 13, wherein a vascular endothelial cell of said vascular endothelial cell vessel undergoes apoptosis.

15. A method of treating an angiogenic-related disorder comprising the steps of:
   (a) identifying a subject exhibiting an angiogenic-related disorder; and
   (b) administering a therapeutically effective amount of a compound comprising a Wnt pathway stimulator and a Tie2 pathway repressor to said subject, wherein the angiogenic-related disorder is treated.

16. The method of claim 15, wherein said angiogenic-related disorder is selected from the group consisting of ocular angiogenic disorders and hyperproliferative disorders.

17. The method of claim 15, wherein said Wnt pathway stimulator is a Wnt7b-like molecule and wherein the Tie2 pathway repressor is an Ang2-1 like molecule.

18. The method of claim 17, wherein said Wnt7b-like molecule is a Wnt7b molecule selected from the group consisting of:
   (a) an isolated polypeptide having an amino acid sequence set forth in SEQ ID NO:2, SEQ ID NO:3, SEQ ID:5, or SEQ ID NO:6; and
   (b) an isolated polypeptide having an amino acid sequence having at least 95% identity to an amino acid sequence set forth in SEQ ID NO:2, SEQ ID NO:3, SEQ ID:5, or SEQ ID NO:6, wherein said polypeptide is capable of interacting with a Fzd4 receptor.

19. The method of claim 17, wherein said Ang2-like molecule is an Ang2 molecule selected from the group consisting of:
   (a) an isolated polypeptide having an amino acid sequence set forth in SEQ ID NO:8, SEQ ID NO:9, SEQ ID:I 1, or SEQ ID NO:12; and
   (b) an isolated polypeptide having an amino acid sequence having at least 95% identity to an amino acid sequence set forth in SEQ ID NO:8, SEQ ID NO:9, SEQ ID:I 1, or SEQ ID NO: 12, wherein said polypeptide is capable of interacting with Tie2.

20. The method of claim 15, wherein said angiogenic-related disorder is a vascular endothelial cell vessel-related disorder.

21. The method of claim 20, wherein a vascular endothelial cell vessel regresses.

22. The method of claim 20, wherein a vascular endothelial cell undergoes apoptosis.

23. A method of regressing capillary bed development comprising the steps of:
   (a) providing a subject in need of capillary bed development regression; and
   (b) administering a vascular endothelial cell vessel regressing compound comprising a Wnt pathway stimulator and a Tie2 pathway repressor to a subject, wherein said capillary bed development regresses.

* * * * *

UNITED STATES PATENT AND TRADEMARK OFFICE
CERTIFICATE OF CORRECTION

PATENT NO. : 7,696,160 B2
APPLICATION NO. : 12/074853
DATED : April 13, 2010
INVENTOR(S) : Richard Lang It is certified that error appears in the above-identified patent and that said Letters Patent is hereby corrected as shown below:

Column 1
Between lines 12 and 13 insert:

--STATEMENT REGARDING FEDERALLY SPONSORED RESEARCH OR DEVELOPMENT
This invention was made with government support under EY010559 and EY015766 awarded by the NIH. The government has certain rights in the invention.--

Signed and Sealed this
Nineteenth Day of March, 2013

Teresa Stanek Rea
*Acting Director of the United States Patent and Trademark Office*

SEQUENCE LISTING

```
<160> NUMBER OF SEQ ID NOS: 12

<210> SEQ ID NO 1
<211> LENGTH: 2544
<212> TYPE: DNA
<213> ORGANISM: Mus musculus
<220> FEATURE:
<221> NAME/KEY: CDS
<222> LOCATION: (481)...(1542)
<223> OTHER INFORMATION: Wnt7b

<400> SEQUENCE: 1
gggtatcccg gccaaggcaa cttgggcaaa ccctgggggc ggcacccgcc gcacactctg      60
gtcaacctcc cctttaaaaa aaacccgccc gcggaggagg cggatgtagg ggcggcctgt     120
ccaatggcag ctgcggcgct ttgggagact tggagacttg agccagagtg agcgacagaa     180
ccggttcgca ccgacagacg gacagaggac cagacagcca ctaaggagcg cttactgccc     240
ccctccgggc ccctgccccg aactccagcc ccagcgcctg ttactgcccc agatacagca     300
agatgcgcgg tcctggcagc gagacacggg cgagcactgt cccccggtcc ccgagccctg     360 gccctagcg cccagcgctg ctgccctgca tcagggaggg ccgcggagac cccagcctca      420
gttggcgcag gagccctgcg ggtggggcct gcccagccca gccaggcgcg ccagcccacc     480 atg ctc ctc ctg tcg ccg cgc agc gcg ctg gtc tcc gtc tat tgc ccg     528
Met Leu Leu Leu Ser Pro Arg Ser Ala Leu Val Ser Val Tyr Cys Pro
 1               5                  10                  15 cag atc ttt ctc ctt ctg tcc agc ggc agt tac cta gca ttg tca tcc     576
Gln Ile Phe Leu Leu Leu Ser Ser Gly Ser Tyr Leu Ala Leu Ser Ser
             20                  25                  30 gtg gtg gcc ctg gga gcc aac atc atc tgc aac aag att cct ggc ctg     624
Val Val Ala Leu Gly Ala Asn Ile Ile Cys Asn Lys Ile Pro Gly Leu
         35                  40                  45 gcc cca cgg cag cgt gcc atc tgc cag agc cga ccc gat gcc atc att     672
Ala Pro Arg Gln Arg Ala Ile Cys Gln Ser Arg Pro Asp Ala Ile Ile
     50                  55                  60
```

| | | |
|---|---|---|
| gtg atc ggg gag ggg gcg cag atg ggc atc gac gag tgc cag cac cag<br>Val Ile Gly Glu Gly Ala Gln Met Gly Ile Asp Glu Cys Gln His Gln<br>65                     70                     75                     80 | | 720 |
| ttc cga ttc ggc cgc tgg aac tgc tcc gcc ctg ggc gag aag acc gtc<br>Phe Arg Phe Gly Arg Trp Asn Cys Ser Ala Leu Gly Glu Lys Thr Val<br>               85                     90                     95 | | 768 |
| ttc ggg caa gaa ctc cga gta ggg agt cga gag gct gcc ttc acc tat<br>Phe Gly Gln Glu Leu Arg Val Gly Ser Arg Glu Ala Ala Phe Thr Tyr<br>              100                    105                   110 | | 816 |
| gcc atc acg gcg gcg ggc gtg gcg cat gct gtc acc gct gcc tgc agc<br>Ala Ile Thr Ala Ala Gly Val Ala His Ala Val Thr Ala Ala Cys Ser<br>         115                    120                   125 | | 864 |
| cag ggc aat ctg agc aat tgt ggc tgt gac cgg gag aag caa ggc tac<br>Gln Gly Asn Leu Ser Asn Cys Gly Cys Asp Arg Glu Lys Gln Gly Tyr<br>130                    135                    140 | | 912 |
| tac aac cag gcg gaa ggc tgg aag tgg ggg ggc tgc tca gcg gac gtc<br>Tyr Asn Gln Ala Glu Gly Trp Lys Trp Gly Gly Cys Ser Ala Asp Val<br>145                    150                    155                   160 | | 960 |
| cgc tac ggc atc gac ttt tct cgt cgc ttt gtg gat gcc cgt gag atc<br>Arg Tyr Gly Ile Asp Phe Ser Arg Arg Phe Val Asp Ala Arg Glu Ile<br>                   165                    170                   175 | | 1008 |
| aaa aag aac gcc agg cgc ctc atg aac ctt cac aac aat gag gcg ggc<br>Lys Lys Asn Ala Arg Arg Leu Met Asn Leu His Asn Asn Glu Ala Gly<br>         180                    185                   190 | | 1056 |
| aga aag gtt ctg gag gac cgc atg aag ctg gaa tgt aag tgt cac ggt<br>Arg Lys Val Leu Glu Asp Arg Met Lys Leu Glu Cys Lys Cys His Gly<br>              195                    200                   205 | | 1104 |
| gtg tca ggc tcc tgt acc acc aaa act tgc tgg acc acg cta cct aag<br>Val Ser Gly Ser Cys Thr Thr Lys Thr Cys Trp Thr Thr Leu Pro Lys<br>210                    215                    220 | | 1152 |
| ttc cgc gag gtg ggc cac ctg ctc aag gag aag tac aac gca gcg gtg<br>Phe Arg Glu Val Gly His Leu Leu Lys Glu Lys Tyr Asn Ala Ala Val<br>225                    230                    235                   240 | | 1200 |
| cag gtg gag gtg gtg cga gcc agc cgc ctg cgc cag ccc acc ttc ctg<br>Gln Val Glu Val Val Arg Ala Ser Arg Leu Arg Gln Pro Thr Phe Leu<br>                   245                    250                   255 | | 1248 |
| cgc atc aag cag cta cgc agc tac cag aag cct atg gag acg gac ctg<br>Arg Ile Lys Gln Leu Arg Ser Tyr Gln Lys Pro Met Glu Thr Asp Leu<br>         260                    265                   270 | | 1296 |
| gtg tac atc gag aag tcg ccc aac tac tgc gag gag gac gcg gcc acg<br>Val Tyr Ile Glu Lys Ser Pro Asn Tyr Cys Glu Glu Asp Ala Ala Thr<br>              275                    280                   285 | | 1344 |
| ggc agc gtg ggc acg cag ggc cgt ctg tgc aac cgc acc tcg ccg ggg<br>Gly Ser Val Gly Thr Gln Gly Arg Leu Cys Asn Arg Thr Ser Pro Gly<br>         290                    295                   300 | | 1392 |
| gcc gac ggc tgt gac acc atg tgc tgc ggc cgc ggc tac aac acg cac<br>Ala Asp Gly Cys Asp Thr Met Cys Cys Gly Arg Gly Tyr Asn Thr His<br>305                    310                    315                   320 | | 1440 |
| cag tac acc aag gtg tgg cag tgt aac tgc aaa ttc cac tgg tgt tgc<br>Gln Tyr Thr Lys Val Trp Gln Cys Asn Cys Lys Phe His Trp Cys Cys<br>              325                    330                   335 | | 1488 |
| ttc gtc aag tgc aac acg tgc agc gag cgc acc gag gtc ttc acc tgc<br>Phe Val Lys Cys Asn Thr Cys Ser Glu Arg Thr Glu Val Phe Thr Cys<br>         340                    345                   350 | | 1536 |
| aag tga ggctcccgcg caggcgcgct cggcccctgc cgaccctgcg ccctcgcca<br>Lys  * | | 1592 |
| ttattttgca catccttctt tgcttctgga gctgccagct gcaggcacag gagggtgggg | | 1652 |
| atagaggtgg ggagctcgag atactccagg ctccttccta ctcgctctgt ccccgcccag | | 1712 |

-continued

```
catccaaggt caacgcaatg gtggtctggt acccaatgga gacaaatccc tttacttctc    1772
tttgggaaag tgaaccacaa agggaccatg agactctgag ggtcacctcc ctgcctgtga    1832
ctggacacag aaaggccaca cccaccagtc acactcaaaa cggtttcctg ggctgtttcc    1892
tgccggccct gggcagtgtg gatggatgtt gacaaaatta tttatgtttt cttagcatca    1952
gatgaggact cagtactaac gactgggtag ccagacctaa ccctatttga ggacacccct    2012
ccctcactcc tcccggcccc tccctgcagg gtcctctgct ccttgcagaa ctcgaggatg    2072
tcagaattgg cacggaagct ggctggtggg gggactcctt atcagcacct tgggaggggc    2132
ttggtggccc tacaaggcct gagatggccg cagaggacag ccaatcttcc attccatttg    2192
gagactgtca tgcaaatcaa atgtcccttg tgtcaggctc caggcatgcc tcgtcctctc    2252
cctggtcctt caccctccca gcctgctgcc aacctccacc tccagtttac aaattctctt    2312
ctcctctgga gccaacctga cacccaggac tgccccacag gttcaggaga ggtcagggac    2372
agttgcccca catgacagat ggacagaggg caatctgaag atttactgga gccccacgg    2432 ctctgtgaaa taaatatact gacacagccc catccagccc aactctggaa gttgccaggg   2492
tgatgggagg ctgcaccccc ttttcagtaa aaaaaaaaaa aaaaaaaaa aa            2544
```

<210> SEQ ID NO 2
<211> LENGTH: 353
<212> TYPE: PRT
<213> ORGANISM: Mus musculus

<400> SEQUENCE: 2

```
Met Leu Leu Leu Ser Pro Arg Ser Ala Leu Val Ser Val Tyr Cys Pro
1               5                   10                  15

Gln Ile Phe Leu Leu Ser Ser Gly Ser Tyr Leu Ala Leu Ser Ser
    20                  25                  30

Val Val Ala Leu Gly Ala Asn Ile Ile Cys Asn Lys Ile Pro Gly Leu
    35                  40                  45

Ala Pro Arg Gln Arg Ala Ile Cys Gln Ser Arg Pro Asp Ala Ile Ile
50                  55                  60

Val Ile Gly Glu Gly Ala Gln Met Gly Ile Asp Glu Cys Gln His Gln
65                  70                  75                  80

Phe Arg Phe Gly Arg Trp Asn Cys Ser Ala Leu Gly Glu Lys Thr Val
            85                  90                  95

Phe Gly Gln Glu Leu Arg Val Gly Ser Arg Glu Ala Ala Phe Thr Tyr
        100                 105                 110

Ala Ile Thr Ala Ala Gly Val Ala His Ala Val Thr Ala Ala Cys Ser
    115                 120                 125

Gln Gly Asn Leu Ser Asn Cys Gly Cys Asp Arg Glu Lys Gln Gly Tyr
130                 135                 140

Tyr Asn Gln Ala Glu Gly Trp Lys Trp Gly Gly Cys Ser Ala Asp Val
145                 150                 155                 160

Arg Tyr Gly Ile Asp Phe Ser Arg Arg Phe Val Asp Ala Arg Glu Ile
            165                 170                 175

Lys Lys Asn Ala Arg Arg Leu Met Asn Leu His Asn Asn Glu Ala Gly
        180                 185                 190

Arg Lys Val Leu Glu Asp Arg Met Lys Leu Glu Cys Lys Cys His Gly
    195                 200                 205

Val Ser Gly Ser Cys Thr Thr Lys Thr Cys Trp Thr Thr Leu Pro Lys
210                 215                 220
```

```
Phe Arg Glu Val Gly His Leu Leu Lys Glu Lys Tyr Asn Ala Ala Val
225                 230                 235                 240

Gln Val Glu Val Val Arg Ala Ser Arg Leu Arg Gln Pro Thr Phe Leu
245                 250                 255

Arg Ile Lys Gln Leu Arg Ser Tyr Gln Lys Pro Met Glu Thr Asp Leu
260                 265                 270

Val Tyr Ile Glu Lys Ser Pro Asn Tyr Cys Glu Asp Ala Ala Thr
275                 280                 285

Gly Ser Val Gly Thr Gln Gly Arg Leu Cys Asn Arg Thr Ser Pro Gly
290                 295                 300

Ala Asp Gly Cys Asp Thr Met Cys Cys Gly Arg Gly Tyr Asn Thr His
305                 310                 315                 320

Gln Tyr Thr Lys Val Trp Gln Cys Asn Cys Lys Phe His Trp Cys Cys
325                 330                 335

Phe Val Lys Cys Asn Thr Cys Ser Glu Arg Thr Glu Val Phe Thr Cys
340                 345                 350

Lys

<210> SEQ ID NO 3
<211> LENGTH: 353
<212> TYPE: PRT
<213> ORGANISM: Mus musculus

<400> SEQUENCE: 3

Met Leu Leu Leu Ser Pro Arg Ser Ala Leu Val Ser Val Tyr Cys Pro
1               5                   10                  15

Gln Ile Phe Leu Leu Ser Ser Gly Ser Tyr Leu Ala Leu Ser Ser
20                  25                  30

Val Val Ala Leu Gly Ala Asn Ile Ile Cys Asn Lys Ile Pro Gly Leu
35                  40                  45

Ala Pro Arg Gln Arg Ala Ile Cys Gln Ser Arg Pro Asp Ala Ile Ile
50                  55                  60

Val Ile Gly Glu Gly Ala Gln Met Gly Ile Asp Glu Cys Gln His Gln
65                  70                  75                  80

Phe Arg Phe Gly Arg Trp Asn Cys Ser Ala Leu Gly Glu Lys Thr Val
85                  90                  95

Phe Gly Gln Glu Leu Arg Val Gly Ser Arg Glu Ala Ala Phe Thr Tyr
100                 105                 110

Ala Ile Thr Ala Ala Gly Val Ala His Ala Val Thr Ala Ala Cys Ser
115                 120                 125

Gln Gly Asn Leu Ser Asn Cys Gly Cys Asp Arg Glu Lys Gln Gly Tyr
130                 135                 140

Tyr Asn Gln Ala Glu Gly Trp Lys Trp Gly Cys Ser Ala Asp Val
145                 150                 155                 160

Arg Tyr Gly Ile Asp Phe Ser Arg Arg Phe Val Asp Ala Arg Glu Ile
165                 170                 175

Lys Lys Asn Ala Arg Arg Leu Met Asn Leu His Asn Asn Glu Ala Gly
180                 185                 190

Arg Lys Val Leu Glu Asp Arg Met Lys Leu Glu Cys Lys Cys His Gly
195                 200                 205

Val Ser Gly Ser Cys Thr Thr Lys Thr Cys Trp Thr Thr Leu Pro Lys
210                 215                 220

Phe Arg Glu Val Gly His Leu Leu Lys Glu Lys Tyr Asn Ala Ala Val
225                 230                 235                 240
```

```
Gln Val Glu Val Val Arg Ala Ser Arg Leu Arg Gln Pro Thr Phe Leu
245                 250                 255
Arg Ile Lys Gln Leu Arg Ser Tyr Gln Lys Pro Met Glu Thr Asp Leu
260                 265                 270
Val Tyr Ile Glu Lys Ser Pro Asn Tyr Cys Glu Glu Asp Ala Ala Thr
275                 280                 285
Gly Ser Val Gly Thr Gln Gly Arg Leu Cys Asn Arg Thr Ser Pro Gly
290                 295                 300
Ala Asp Gly Cys Asp Thr Met Cys Cys Gly Arg Gly Tyr Asn Thr His
305                 310                 315                 320
Gln Tyr Thr Lys Val Trp Gln Cys Asn Cys Lys Phe His Trp Cys Cys
325                 330                 335
Phe Val Lys Cys Asn Thr Cys Ser Glu Arg Thr Glu Val Phe Thr Cys
340                 345                 350
Lys

<210> SEQ ID NO 4
<211> LENGTH: 2160
<212> TYPE: DNA
<213> ORGANISM: Homo sapiens
<220> FEATURE:
<221> NAME/KEY: CDS
<222> LOCATION: (6)...(1055)
<223> OTHER INFORMATION: Wnt7b

<400> SEQUENCE: 4 ggatc atg cac aga aac ttt cgc aag tgg att ttc tac gtg ttt ctc tgc       50
      Met His Arg Asn Phe Arg Lys Trp Ile Phe Tyr Val Phe Leu Cys
      1               5                   10                  15 ttt ggc gtc ctg tac gtg aag ctc gga gca ctg tca tcc gtg gtg gcc        98
Phe Gly Val Leu Tyr Val Lys Leu Gly Ala Leu Ser Ser Val Val Ala
            20                  25                  30 ctg gga gcc aac atc atc tgc aac aag att cct ggc cta gcc ccg cgg       146
Leu Gly Ala Asn Ile Ile Cys Asn Lys Ile Pro Gly Leu Ala Pro Arg
        35                  40                  45 cag cgt gcc atc tgc cag agt cgg ccc gat gcc atc att gtg att ggg       194
Gln Arg Ala Ile Cys Gln Ser Arg Pro Asp Ala Ile Ile Val Ile Gly
    50                  55                  60 gag ggg gcg cag atg ggc atc aac gag tgc cag tac cag ttc cgc ttc       242
Glu Gly Ala Gln Met Gly Ile Asn Glu Cys Gln Tyr Gln Phe Arg Phe
65                  70                  75 gga cgc tgg aac tgc tct gcc ctc ggc gag aag acc gtc ttc ggg caa       290
Gly Arg Trp Asn Cys Ser Ala Leu Gly Glu Lys Thr Val Phe Gly Gln
            80                  85                  90                  95 gag ctc cga gta ggg agc cgt gag gct gcc ttc acg tac gcc atc acc       338
Glu Leu Arg Val Gly Ser Arg Glu Ala Ala Phe Thr Tyr Ala Ile Thr
                100                 105                 110 gcg gct ggc gtg gcg cac gcc gtc acc gct gcc tgc agc caa ggg aac       386
Ala Ala Gly Val Ala His Ala Val Thr Ala Ala Cys Ser Gln Gly Asn
            115                 120                 125 ctg agc aac tgc ggc tgc gac cgc gag aag cag ggc tac tac aac caa       434
Leu Ser Asn Cys Gly Cys Asp Arg Glu Lys Gln Gly Tyr Tyr Asn Gln
        130                 135                 140 gcc gag ggc tgg aag tgg ggc ggc tgc tcg gcc gac gtg cgt tac ggc       482
Ala Glu Gly Trp Lys Trp Gly Gly Cys Ser Ala Asp Val Arg Tyr Gly
    145                 150                 155 atc gac ttc tcc cgg cgc ttc gtg gac gct cgg gag atc aag aag aac       530
Ile Asp Phe Ser Arg Arg Phe Val Asp Ala Arg Glu Ile Lys Lys Asn
160                 165                 170                 175
```

-continued

| | | |
|---|---|---|
| gcg cgg cgc ctc atg aac ctg cat aac aat gag gcc ggc agg aag gtt<br>Ala Arg Arg Leu Met Asn Leu His Asn Asn Glu Ala Gly Arg Lys Val<br>180                           185                           190 | 578 |

```
gcg cgg cgc ctc atg aac ctg cat aac aat gag gcc ggc agg aag gtt     578
Ala Arg Arg Leu Met Asn Leu His Asn Asn Glu Ala Gly Arg Lys Val
                180                 185                 190 cta gag gac cgg atg cag ctg gag tgc aag tgc cac ggc gtg tct ggc     626
Leu Glu Asp Arg Met Gln Leu Glu Cys Lys Cys His Gly Val Ser Gly
            195                 200                 205 tcc tgc acc acc aaa acc tgc tgg acc acg ctg ccc aag ttc cga gag     674
Ser Cys Thr Thr Lys Thr Cys Trp Thr Thr Leu Pro Lys Phe Arg Glu
        210                 215                 220 gtg ggc cac ctg ctg aag gag aag tac aac gcg gcc gtg cag gtg gag     722
Val Gly His Leu Leu Lys Glu Lys Tyr Asn Ala Ala Val Gln Val Glu
    225                 230                 235 gtg gtg cgg gcc agc cgt ctg cgg cag ccc acc ttc ctg cgc atc aaa     770
Val Val Arg Ala Ser Arg Leu Arg Gln Pro Thr Phe Leu Arg Ile Lys
240                 245                 250                 255 cag ctg cgc agc tat cag aag ccc atg gag aca gac ctg gtg tac att     818
Gln Leu Arg Ser Tyr Gln Lys Pro Met Glu Thr Asp Leu Val Tyr Ile
                260                 265                 270 gag aag tcg ccc aac tac tgc gag gag gac gcg gcc acg ggc agc gtg     866
Glu Lys Ser Pro Asn Tyr Cys Glu Glu Asp Ala Ala Thr Gly Ser Val
            275                 280                 285 ggc acg cag ggc cgt ctc tgc aac cgc acg tcg ccc ggc gcg gac ggc     914
Gly Thr Gln Gly Arg Leu Cys Asn Arg Thr Ser Pro Gly Ala Asp Gly
        290                 295                 300 tgt gac acc atg tgc tgc gga cga ggc tac aac acc cac cag tac acc     962
Cys Asp Thr Met Cys Cys Gly Arg Gly Tyr Asn Thr His Gln Tyr Thr
    305                 310                 315 aag gtg tgg cag tgc aac tgc aaa ttc cac tgg tgc tgc ttc gtc aag    1010
Lys Val Trp Gln Cys Asn Cys Lys Phe His Trp Cys Cys Phe Val Lys
320                 325                 330                 335 tgc aac acc tgc agc gag cgc acc gag gtc ttc acc tgc aag tga        1055
Cys Asn Thr Cys Ser Glu Arg Thr Glu Val Phe Thr Cys Lys  *
                340                 345 ggccaggccc ggaggcggcc gcgggcaccc tggaacccgg cggcattttg cacatccact  1115
cctcaccttc cctgccttgg tgctgccagc agcagacata gacgggtgca gaagcgggga  1175
gctccaggtg caggagggca ccggccgggg cccacgccct ctgcccgcct ccctggggct  1235
ccttcctgcc acctcctccc atcacctcct gcggcagaac agcacccgtg acccacccag  1295
agagcaaggc caggggtctt ggtgctcccc gacgggccc ggcaagttct ctttcttctc   1355
tctgggaaaa tgaacgtcca ggacacacct gtatcccaga gagcaaagtg atgaggagac  1415
tgagcgtccc cagccccacc tggcggcatg gacacagaaa agctacgccg gctggcctct  1475
ccagaccagt tccaggctg gtctgccgc tgggccctgg ggcggtgggg acagatgttg    1535
acacaaatta tttatgtttt cttagtatca gaagaggatt ctcggcacta acacatagcc  1595
agtcctaact ccgtactctg tgtcagccca tccctagac accctctgtt tcctttcccg   1655
gccccacctg gccggccctc tgcccctgca gagctgaggc agcctgggt tgatggggac   1715
cacgcggtgc ctgcaggtcc tagaagtgag ctgggcaggg gctcttcaga ccacacagcc  1775
ctgaccgggc cttggaggag agccatggac aggctcctcc atgccgtctt tccttctttt  1835
gaaaatccta tcaatggctg ggcgcggtgg ctcacacctg taatcccagc actttgggag  1895
accgaggcag gtggatcacc tgaggtcagg agttcgagac cagcctggcc aacgtggtga  1955
aaccctgtct ctactaaaaa tacaaaaatt agctgggcgt ggtggcgtgc acctgtaatc  2015
ccagctactc aggaggctga gacaggacac ttgcttgaac ccgggaggtg gaggttgcaa  2075
```

```
tgagccaaga ttgtgccact gtattccaac ttgggtgaca gagcacgact ctgtctcaaa    2135
aaaaaaaaaa aaaaaaaaaa aaaaa                                          2160

<210> SEQ ID NO 5
<211> LENGTH: 349
<212> TYPE: PRT
<213> ORGANISM: Homo sapiens

<400> SEQUENCE: 5

Met His Arg Asn Phe Arg Lys Trp Ile Phe Tyr Val Phe Leu Cys Phe
1               5                   10                  15

Gly Val Leu Tyr Val Lys Leu Gly Ala Leu Ser Ser Val Val Ala Leu
            20                  25                  30

Gly Ala Asn Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ala Gln Met Gly Ile Asn Glu Cys Gln Tyr Gln Phe Arg Phe Gly
65                  70                  75                  80

Arg Trp Asn Cys Ser Ala Leu Gly Glu Lys Thr Val Phe Gly Gln Glu
                85                  90                  95

Leu Arg Val Gly Ser Arg Glu Ala Ala Phe Thr Tyr Ala Ile Thr Ala
            100                 105                 110

Ala Gly Val Ala His Ala Val Thr Ala Ala Cys Ser Gln Gly Asn Leu
        115                 120                 125

Ser Asn Cys Gly Cys Asp Arg Glu Lys Gln Gly Tyr Tyr Asn Gln Ala
    130                 135                 140

Glu Gly Trp Lys Trp Gly Gly Cys Ser Ala Asp Val Arg Tyr Gly Ile
145                 150                 155                 160

Asp Phe Ser Arg Arg Phe Val Asp Ala Arg Glu Ile Lys Lys Asn Ala
                165                 170                 175

Arg Arg Leu Met Asn Leu His Asn Asn Glu Ala Gly Arg Lys Val Leu
            180                 185                 190

Glu Asp Arg Met Gln Leu Glu Cys Lys Cys His Gly Val Ser Gly Ser
        195                 200                 205

Cys Thr Thr Lys Thr Cys Trp Thr Thr Leu Pro Lys Phe Arg Glu Val
    210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
                245                 250                 255

Leu Arg Ser Tyr Gln Lys Pro Met Glu Thr Asp Leu Val Tyr Ile Glu
            260                 265                 270

Lys Ser Pro Asn Tyr Cys Glu Glu Asp Ala Ala Thr Gly Ser Val Gly
        275                 280                 285

Thr Gln Gly Arg Leu Cys Asn Arg Thr Ser Pro Gly Ala Asp Gly Cys
    290                 295                 300

Asp Thr Met Cys Cys Gly Arg Gly Tyr Asn Thr His Gln Tyr Thr Lys
305                 310                 315                 320

Val Trp Gln Cys Asn Cys Lys Phe His Trp Cys Cys Phe Val Lys Cys
                325                 330                 335

Asn Thr Cys Ser Glu Arg Thr Glu Val Phe Thr Cys Lys
            340                 345
```

<210> SEQ ID NO 6
<211> LENGTH: 349
<212> TYPE: PRT
<213> ORGANISM: Homo sapiens

<400> SEQUENCE: 6

```
Met His Arg Asn Phe Arg Lys Trp Ile Phe Tyr Val Phe Leu Cys Phe
1               5                   10                  15

Gly Val Leu Tyr Val Lys Leu Gly Ala Leu Ser Ser Val Val Ala Leu
            20                  25                  30

Gly Ala Asn Ile Ile Cys Asn Lys Ile Pro Gly Leu Ala Pro Arg Gln
        35                  40                  45

Arg Ala Ile Cys Gln Ser Arg Pro Asp Ala Ile Val Ile Gly Glu
    50                  55                  60

Gly Ala Gln Met Gly Ile Asn Glu Cys Gln Tyr Gln Phe Arg Phe Gly
65                  70                  75                  80

Arg Trp Asn Cys Ser Ala Leu Gly Glu Lys Thr Val Phe Gly Gln Glu
                85                  90                  95

Leu Arg Val Gly Ser Arg Glu Ala Ala Phe Thr Tyr Ala Ile Thr Ala
            100                 105                 110

Ala Gly Val Ala His Ala Val Thr Ala Ala Cys Ser Gln Gly Asn Leu
        115                 120                 125

Ser Asn Cys Gly Cys Asp Arg Glu Lys Gln Gly Tyr Tyr Asn Gln Ala
    130                 135                 140

Glu Gly Trp Lys Trp Gly Gly Cys Ser Ala Asp Val Arg Tyr Gly Ile
145                 150                 155                 160

Asp Phe Ser Arg Arg Phe Val Asp Ala Arg Glu Ile Lys Lys Asn Ala
                165                 170                 175

Arg Arg Leu Met Asn Leu His Asn Asn Glu Ala Gly Arg Lys Val Leu
            180                 185                 190

Glu Asp Arg Met Gln Leu Glu Cys Lys Cys His Gly Val Ser Gly Ser
        195                 200                 205

Cys Thr Thr Lys Thr Cys Trp Thr Thr Leu Pro Lys Phe Arg Glu Val
    210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
                245                 250                 255

Leu Arg Ser Tyr Gln Lys Pro Met Glu Thr Asp Leu Val Tyr Ile Glu
            260                 265                 270

Lys Ser Pro Asn Tyr Cys Glu Glu Asp Ala Ala Thr Gly Ser Val Gly
        275                 280                 285

Thr Gln Gly Arg Leu Cys Asn Arg Thr Ser Pro Gly Ala Asp Gly Cys
    290                 295                 300

Asp Thr Met Cys Cys Gly Arg Gly Tyr Asn Thr His Gln Tyr Thr Lys
305                 310                 315                 320

Val Trp Gln Cys Asn Cys Lys Phe His Trp Cys Cys Phe Val Lys Cys
                325                 330                 335

Asn Thr Cys Ser Glu Arg Thr Glu Val Phe Thr Cys Lys
            340                 345
```

<210> SEQ ID NO 7
<211> LENGTH: 2475
<212> TYPE: DNA
<213> ORGANISM: Mus musculus

```
<220> FEATURE:
<221> NAME/KEY: CDS
<222> LOCATION: (274)...(1764)
<223> OTHER INFORMATION: Angiopoietin 2

<400> SEQUENCE: 7
```

| | |
|---|---:|
| gatactgaca ctgtagactc aggggagaaa caaagagtcc gtgcagacct ctggagtgag | 60 |
| cagggctgct ccttcctctc aggacagctc cgagtgtgcc ggggagaaga aagagaaga | 120 |
| gacaggcact gggaaagagc ctgctgcggg acggagaagg ctctcactga tggacttatt | 180 |
| cacacggcac agccctgtgc cttagacagc agctgagagc tcaggacgca agtttgctga | 240 |
| actcacagtt tagaacccaa aagagagag aga atg tgg cag atc att ttc cta | 294 |
|                                                    Met Trp Gln Ile Ile Phe Leu<br>                                                   1             5 | |
| act ttt ggc tgg gat ctt gtc ttg gcc tca gcc tac agt aac ttt agg<br>Thr Phe Gly Trp Asp Leu Val Leu Ala Ser Ala Tyr Ser Asn Phe Arg<br>          10                 15                   20 | 342 |
| aag agc gtg gac agc aca ggc aga agg cag tac cag gtc cag aac gga<br>Lys Ser Val Asp Ser Thr Gly Arg Arg Gln Tyr Gln Val Gln Asn Gly<br>25                      30                   35 | 390 |
| ccc tgc agc tac acg ttc ctg ctg ccg gag acc gac agc tgc cga tct<br>Pro Cys Ser Tyr Thr Phe Leu Leu Pro Glu Thr Asp Ser Cys Arg Ser<br>40                   45                   50                 55 | 438 |
| tcc tcc agc ccc tac atg tcc aat gcc gtg cag agg gat gca ccc ctc<br>Ser Ser Ser Pro Tyr Met Ser Asn Ala Val Gln Arg Asp Ala Pro Leu<br>                   60                   65                   70 | 486 |
| gac tac gac gac tca gtg caa agg ctg cag gtg ctg gag aac att cta<br>Asp Tyr Asp Asp Ser Val Gln Arg Leu Gln Val Leu Glu Asn Ile Leu<br>                 75                   80                 85 | 534 |
| gag aac aac aca cag tgg ctg atg aag ctg gag aat tac att cag gac<br>Glu Asn Asn Thr Gln Trp Leu Met Lys Leu Glu Asn Tyr Ile Gln Asp<br> 90                   95                   100 | 582 |
| aac atg aag aag gag atg gtg gag atc caa cag aat gtg gtg cag aac<br>Asn Met Lys Lys Glu Met Val Glu Ile Gln Gln Asn Val Val Gln Asn<br>105                   110                  115 | 630 |
| cag aca gct gtg atg ata gag att gga acc agc ttg ctg aac cag aca<br>Gln Thr Ala Val Met Ile Glu Ile Gly Thr Ser Leu Leu Asn Gln Thr<br>120                   125                  130                  135 | 678 |
| gca gca caa act cgg aaa ctg act gat gtg gaa gcc caa gta cta aac<br>Ala Ala Gln Thr Arg Lys Leu Thr Asp Val Glu Ala Gln Val Leu Asn<br>                   140                  145                  150 | 726 |
| cag acg aca aga ctc gag ctg cag ctt ctc caa cat tct att tct acc<br>Gln Thr Thr Arg Leu Glu Leu Gln Leu Leu Gln His Ser Ile Ser Thr<br>                   155                  160                  165 | 774 |
| aac aaa ttg gaa aag cag att ttg gat cag acc agt gaa ata aac aag<br>Asn Lys Leu Glu Lys Gln Ile Leu Asp Gln Thr Ser Glu Ile Asn Lys<br>170                   175                  180 | 822 |
| cta caa aat aag aac agc ttc cta gaa cag aaa gtt ctg gac atg gag<br>Leu Gln Asn Lys Asn Ser Phe Leu Glu Gln Lys Val Leu Asp Met Glu<br>         185                  190                  195 | 870 |
| ggc aag cac agc gag cag cta cag tcc atg aag gag cag aag gac gag<br>Gly Lys His Ser Glu Gln Leu Gln Ser Met Lys Glu Gln Lys Asp Glu<br>200                   205                  210                  215 | 918 |
| ctc cag gtg ctg gtg tcc aag cag agc tct gtc att gac gag ctg gag<br>Leu Gln Val Leu Val Ser Lys Gln Ser Ser Val Ile Asp Glu Leu Glu<br>                   220                  225                  230 | 966 |
| aag aag ctg gtg aca gcc acg gtc aac aac tcg ctc ctt cag aag cag<br>Lys Lys Leu Val Thr Ala Thr Val Asn Asn Ser Leu Leu Gln Lys Gln<br>235                   240                  245 | 1014 |

```
cag cat gac cta atg gag acc gtc aac agc ttg ctg acc atg atg tca      1062
Gln His Asp Leu Met Glu Thr Val Asn Ser Leu Leu Thr Met Met Ser
        250                 255                 260 tca ccc aac tcc aag agc tcg gtt gct atc cgt aaa gaa gag caa acc      1110
Ser Pro Asn Ser Lys Ser Ser Val Ala Ile Arg Lys Glu Glu Gln Thr
265                 270                 275 acc ttc aga gac tgt gcg gaa atc ttc aag tca gga ctc acc acc agt      1158
Thr Phe Arg Asp Cys Ala Glu Ile Phe Lys Ser Gly Leu Thr Thr Ser
280                 285                 290                 295 ggc atc tac aca ctg acc ttc ccc aac tcc aca gag gag atc aag gcc      1206
Gly Ile Tyr Thr Leu Thr Phe Pro Asn Ser Thr Glu Glu Ile Lys Ala
                300                 305                 310 tac tgt gac atg gac gtg ggt gga gga ggg tgg aca gtc atc caa cac      1254
Tyr Cys Asp Met Asp Val Gly Gly Gly Gly Trp Thr Val Ile Gln His
                315                 320                 325 cga gaa gat ggc agt gtg gac ttc cag agg acg tgg aaa gaa tac aaa      1302
Arg Glu Asp Gly Ser Val Asp Phe Gln Arg Thr Trp Lys Glu Tyr Lys
                330                 335                 340 gag ggc ttc ggg agc cct ctg gga gag tac tgg ctg ggc aat gag ttt      1350
Glu Gly Phe Gly Ser Pro Leu Gly Glu Tyr Trp Leu Gly Asn Glu Phe
345                 350                 355 gtc tcc cag ctg acc ggt cag cac cgc tac gtg ctt aag atc cag ctg      1398
Val Ser Gln Leu Thr Gly Gln His Arg Tyr Val Leu Lys Ile Gln Leu
360                 365                 370                 375 aag gac tgg gaa ggc aac gag gcg cat tcg ctg tat gat cac ttc tac      1446
Lys Asp Trp Glu Gly Asn Glu Ala His Ser Leu Tyr Asp His Phe Tyr
                380                 385                 390 ctc gct ggt gaa gag tcc aac tac agg att cac ctt aca gga ctc acg      1494
Leu Ala Gly Glu Glu Ser Asn Tyr Arg Ile His Leu Thr Gly Leu Thr
                395                 400                 405 ggg acc gcg ggc aaa ata agt agc atc agc caa cca gga agt gat ttt      1542
Gly Thr Ala Gly Lys Ile Ser Ser Ile Ser Gln Pro Gly Ser Asp Phe
                410                 415                 420 agc aca aag gat tcg gac aat gac aaa tgc atc tgc aag tgt tcc cag      1590
Ser Thr Lys Asp Ser Asp Asn Asp Lys Cys Ile Cys Lys Cys Ser Gln
425                 430                 435 atg ctc tca gga ggc tgg tgg ttt gac gca tgt ggt cct tcc aac ttg      1638
Met Leu Ser Gly Gly Trp Trp Phe Asp Ala Cys Gly Pro Ser Asn Leu
440                 445                 450                 455 aat gga cag tac tac cca caa aaa cag aat aca aat aag ttt aac ggt      1686
Asn Gly Gln Tyr Tyr Pro Gln Lys Gln Asn Thr Asn Lys Phe Asn Gly
                460                 465                 470 atc aag tgg tac tac tgg aag ggg tcc ggc tac tcg ctc aag gcc aca      1734
Ile Lys Trp Tyr Tyr Trp Lys Gly Ser Gly Tyr Ser Leu Lys Ala Thr
                475                 480                 485 acc atg atg atc cgg cca gca gat ttc taa atgcctgcct acactaccag        1784
Thr Met Met Ile Arg Pro Ala Asp Phe *
                490                 495 aagaacttgc tgcatccaaa gattaactcc aaggcactga gagacaccaa tgcatagcag    1844
cccctttcca catcaggaag tgctcctggg ggtgggagg gtctgtgtgt accagactga     1904
agcgcatcac ttaagcctgc accgctaacc aaccaaaggc actgcagtct ggagaaacac    1964
ttctgggaag gttgtggctg aggatcagaa ggacagcgtg cagactctgt cacagggaag    2024
aatgttccgt gggagttcag cagtaaataa ctggaaaaca gaacacttag atggtgcaga    2084
taaatcttgg gaccacattc ctctaagcac ggtttctaga gtgaatacat tcacagctcg    2144
gctgtcacaa tgacaaggcc gtgtcctcgc actgtggcag ccagtatcca gggatttcta    2204
agtggtgggc acaggttatc atctggagaa gcacacattc attgttttcc tcttgggtgc    2264
```

-continued

```
tttacatgtt catttgaaaa caacacattt acctatcttg atggcttagt ttttaatggc    2324
tggctactat ttactatatg gcaaaaatgc ccacatctct ggaataacca ccaaataagc    2384
gccatgttgg tgaatgcgga gactgtacta ttttgttttc ttcctggctg ttaaatatga    2444
aggtattttt agtaattaaa tataagttat t                                   2475

<210> SEQ ID NO 8
<211> LENGTH: 496
<212> TYPE: PRT
<213> ORGANISM: Mus musculus

<400> SEQUENCE: 8

Met Trp Gln Ile Ile Phe Leu Thr Phe Gly Trp Asp Leu Val Leu Ala
1               5                   10                  15

Ser Ala Tyr Ser Asn Phe Arg Lys Ser Val Asp Ser Thr Gly Arg Arg
            20                  25                  30

Gln Tyr Gln Val Gln Asn Gly Pro Cys Ser Tyr Thr Phe Leu Leu Pro
        35                  40                  45

Glu Thr Asp Ser Cys Arg Ser Ser Ser Pro Tyr Met Ser Asn Ala
    50                  55                  60

Val Gln Arg Asp Ala Pro Leu Asp Tyr Asp Asp Ser Val Gln Arg Leu
65                  70                  75                  80

Gln Val Leu Glu Asn Ile Leu Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Val Val Gln Asn Gln Thr Ala Val Met Ile Glu Ile Gly
        115                 120                 125

Thr Ser Leu Leu Asn Gln Thr Ala Ala Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Gln His Ser Ile Ser Thr Asn Lys Leu Glu Lys Gln Ile Leu Asp
                165                 170                 175

Gln Thr Ser Glu Ile Asn Lys Leu Gln Asn Lys Asn Ser Phe Leu Glu
            180                 185                 190

Gln Lys Val Leu Asp Met Glu Gly Lys His Ser Glu Gln Leu Gln Ser
        195                 200                 205

Met Lys Glu Gln Lys Asp Glu Leu Gln Val Leu Val Ser Lys Gln Ser
    210                 215                 220

Ser Val Ile Asp Glu Leu Glu Lys Lys Leu Val Thr Ala Thr Val Asn
225                 230                 235                 240

Asn Ser Leu Leu Gln Lys Gln Gln His Asp Leu Met Glu Thr Val Asn
                245                 250                 255

Ser Leu Leu Thr Met Met Ser Ser Pro Asn Ser Lys Ser Ser Val Ala
            260                 265                 270

Ile Arg Lys Glu Glu Gln Thr Thr Phe Arg Asp Cys Ala Glu Ile Phe
        275                 280                 285

Lys Ser Gly Leu Thr Thr Ser Gly Ile Tyr Thr Leu Thr Phe Pro Asn
    290                 295                 300

Ser Thr Glu Glu Ile Lys Ala Tyr Cys Asp Met Asp Val Gly Gly Gly
305                 310                 315                 320

Gly Trp Thr Val Ile Gln His Arg Glu Asp Gly Ser Val Asp Phe Gln
                325                 330                 335
```

```
Arg Thr Trp Lys Glu Tyr Lys Glu Gly Phe Gly Ser Pro Leu Gly Glu
340                 345                 350

Tyr Trp Leu Gly Asn Glu Phe Val Ser Gln Leu Thr Gly Gln His Arg
355                 360                 365

Tyr Val Leu Lys Ile Gln Leu Lys Asp Trp Glu Gly Asn Glu Ala His
370                 375                 380

Ser Leu Tyr Asp His Phe Tyr Leu Ala Gly Glu Glu Ser Asn Tyr Arg
385                 390                 395                 400

Ile His Leu Thr Gly Leu Thr Gly Thr Ala Gly Lys Ile Ser Ser Ile
405                 410                 415

Ser Gln Pro Gly Ser Asp Phe Ser Thr Lys Asp Ser Asp Asn Asp Lys
420                 425                 430

Cys Ile Cys Lys Cys Ser Gln Met Leu Ser Gly Gly Trp Trp Phe Asp
435                 440                 445

Ala Cys Gly Pro Ser Asn Leu Asn Gly Gln Tyr Tyr Pro Gln Lys Gln
450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
485                 490                 495

<210> SEQ ID NO 9
<211> LENGTH: 496
<212> TYPE: PRT
<213> ORGANISM: Mus musculus

<400> SEQUENCE: 9

Met Trp Gln Ile Ile Phe Leu Thr Phe Gly Trp Asp Leu Val Leu Ala
1               5                   10                  15

Ser Ala Tyr Ser Asn Phe Arg Lys Ser Val Asp Ser Thr Gly Arg Arg
20                  25                  30

Gln Tyr Gln Val Gln Asn Gly Pro Cys Ser Tyr Thr Phe Leu Leu Pro
35                  40                  45

Glu Thr Asp Ser Cys Arg Ser Ser Ser Pro Tyr Met Ser Asn Ala
50                  55                  60

Val Gln Arg Asp Ala Pro Leu Asp Tyr Asp Asp Ser Val Gln Arg Leu
65                  70                  75                  80

Gln Val Leu Glu Asn Ile Leu Glu Asn Asn Thr Gln Trp Leu Met Lys
85                  90                  95

Leu Glu Asn Tyr Ile Gln Asp Asn Met Lys Lys Glu Met Val Glu Ile
100                 105                 110

Gln Gln Asn Val Val Gln Asn Gln Thr Ala Val Met Ile Glu Ile Gly
115                 120                 125

Thr Ser Leu Leu Asn Gln Thr Ala Ala Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Gln His Ser Ile Ser Thr Asn Lys Leu Glu Lys Gln Ile Leu Asp
165                 170                 175

Gln Thr Ser Glu Ile Asn Lys Leu Gln Asn Lys Asn Ser Phe Leu Glu
180                 185                 190

Gln Lys Val Leu Asp Met Glu Gly Lys His Ser Glu Gln Leu Gln Ser
195                 200                 205

Met Lys Glu Gln Lys Asp Glu Leu Gln Val Leu Val Ser Lys Gln Ser
210                 215                 220
```

```
Ser Val Ile Asp Glu Leu Glu Lys Lys Leu Val Thr Ala Thr Val Asn
225                 230                 235                 240

Asn Ser Leu Leu Gln Lys Gln Gln His Asp Leu Met Glu Thr Val Asn
245                 250                 255

Ser Leu Leu Thr Met Met Ser Ser Pro Asn Ser Lys Ser Ser Val Ala
260                 265                 270

Ile Arg Lys Glu Glu Gln Thr Thr Phe Arg Asp Cys Ala Glu Ile Phe
275                 280                 285

Lys Ser Gly Leu Thr Thr Ser Gly Ile Tyr Thr Leu Thr Phe Pro Asn
290                 295                 300

Ser Thr Glu Glu Ile Lys Ala Tyr Cys Asp Met Asp Val Gly Gly Gly
305                 310                 315                 320

Gly Trp Thr Val Ile Gln His Arg Glu Asp Gly Ser Val Asp Phe Gln
325                 330                 335

Arg Thr Trp Lys Glu Tyr Lys Glu Gly Phe Gly Ser Pro Leu Gly Glu
340                 345                 350

Tyr Trp Leu Gly Asn Glu Phe Val Ser Gln Leu Thr Gly Gln His Arg
355                 360                 365

Tyr Val Leu Lys Ile Gln Leu Lys Asp Trp Glu Gly Asn Glu Ala His
370                 375                 380

Ser Leu Tyr Asp His Phe Tyr Leu Ala Gly Glu Glu Ser Asn Tyr Arg
385                 390                 395                 400

Ile His Leu Thr Gly Leu Thr Gly Thr Ala Gly Lys Ile Ser Ser Ile
405                 410                 415

Ser Gln Pro Gly Ser Asp Phe Ser Thr Lys Asp Ser Asp Asn Asp Lys
420                 425                 430

Cys Ile Cys Lys Cys Ser Gln Met Leu Ser Gly Gly Trp Trp Phe Asp
435                 440                 445

Ala Cys Gly Pro Ser Asn Leu Asn Gly Gln Tyr Tyr Pro Gln Lys Gln
450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
485                 490                 495

<210> SEQ ID NO 10
<211> LENGTH: 2269
<212> TYPE: DNA
<213> ORGANISM: Homo sapiens
<220> FEATURE:
<221> NAME/KEY: CDS
<222> LOCATION: (350)...(1840)
<223> OTHER INFORMATION: Angiopoietin 2

<400> SEQUENCE: 10
tgggttggtg tttatctcct cccagccttg agggagggaa caacactgta ggatctgggg      60
agagaggaac aaaggaccgt gaaagctgct ctgtaaaagc tgacacagcc ctcccaagtg     120
agcaggactt tcttcccac tgcaatctga cagtttactg catgcctgga gaaacacag      180 cagtaaaaac caggtttgct actggaaaaa gaggaaagag aagactttca ttgacggacc     240
cagccatggc agcgtagcag ccctgcgttt cagacggcag cagctcggga ctctggacgt     300
gtgtttgccc tcaagtttgc taagctgctg gtttattact gaagaaaga atg tgg cag     358
                                                      Met Trp Gln
                                                        1
```

```
att gtt ttc ttt act ctg agc tgt gat ctt gtc ttg gcc gca gcc tat      406
Ile Val Phe Phe Thr Leu Ser Cys Asp Leu Val Leu Ala Ala Ala Tyr
  5              10                  15 aac aac ttt cgg aag agc atg gac agc ata gga aag aag caa tat cag      454
Asn Asn Phe Arg Lys Ser Met Asp Ser Ile Gly Lys Lys Gln Tyr Gln
 20              25                  30                  35 gtc cag cat ggg tcc tgc agc tac act ttc ctc ctg cca gag atg gac      502
Val Gln His Gly Ser Cys Ser Tyr Thr Phe Leu Leu Pro Glu Met Asp
             40                  45                  50 aac tgc cgc tct tcc tcc agc ccc tac gtg tcc aat gct gtg cag agg      550
Asn Cys Arg Ser Ser Ser Ser Pro Tyr Val Ser Asn Ala Val Gln Arg
                 55                  60                  65 gac gcg ccg ctc gaa tac gat gac tcg gtg cag agg ctg caa gtg ctg      598
Asp Ala Pro Leu Glu Tyr Asp Asp Ser Val Gln Arg Leu Gln Val Leu
         70                  75                  80 gag aac atc atg gaa aac aac act cag tgg cta atg aag ctt gag aat      646
Glu Asn Ile Met Glu Asn Asn Thr Gln Trp Leu Met Lys Leu Glu Asn
 85                  90                  95 tat atc cag gac aac atg aag aaa gaa atg gta gag ata cag cag aat      694
Tyr Ile Gln Asp Asn Met Lys Lys Glu Met Val Glu Ile Gln Gln Asn
100                 105                 110                 115 gca gta cag aac cag acg gct gtg atg ata gaa ata ggg aca aac ctg      742
Ala Val Gln Asn Gln Thr Ala Val Met Ile Glu Ile Gly Thr Asn Leu
                120                 125                 130 ttg aac caa aca gct gag caa acg cgg aag tta act gat gtg gaa gcc      790
Leu Asn Gln Thr Ala Glu Gln Thr Arg Lys Leu Thr Asp Val Glu Ala
            135                 140                 145 caa gta tta aat cag acc acg aga ctt gaa ctt cag ctc ttg gaa cac      838
Gln Val Leu Asn Gln Thr Thr Arg Leu Glu Leu Gln Leu Leu Glu His
        150                 155                 160 tcc ctc tcg aca aac aaa ttg gaa aaa cag att ttg gac cag acc agt      886
Ser Leu Ser Thr Asn Lys Leu Glu Lys Gln Ile Leu Asp Gln Thr Ser
165                 170                 175 gaa ata aac aaa ttg caa gat aag aac agt ttc cta gaa aag aag gtg      934
Glu Ile Asn Lys Leu Gln Asp Lys Asn Ser Phe Leu Glu Lys Lys Val
180                 185                 190                 195 cta gct atg gaa gac aag cac atc atc caa cta cag tca ata aaa gaa      982
Leu Ala Met Glu Asp Lys His Ile Ile Gln Leu Gln Ser Ile Lys Glu
                200                 205                 210 gag aaa gat cag cta cag gtg tta gta tcc aag caa aat tcc atc att     1030
Glu Lys Asp Gln Leu Gln Val Leu Val Ser Lys Gln Asn Ser Ile Ile
            215                 220                 225 gaa gaa cta gaa aaa aaa ata gtg act gcc acg gtg aat aat tca gtt     1078
Glu Glu Leu Glu Lys Lys Ile Val Thr Ala Thr Val Asn Asn Ser Val
        230                 235                 240 ctt caa aag cag caa cat gat ctc atg gag aca gtt aat aac tta ctg     1126
Leu Gln Lys Gln Gln His Asp Leu Met Glu Thr Val Asn Asn Leu Leu
245                 250                 255 act atg atg tcc aca tca aac tca gct aag gac ccc act gtt gct aaa     1174
Thr Met Met Ser Thr Ser Asn Ser Ala Lys Asp Pro Thr Val Ala Lys
260                 265                 270                 275 gaa gaa caa atc agc ttc aga gac tgt gct gaa gta ttc aaa tca gga     1222
Glu Glu Gln Ile Ser Phe Arg Asp Cys Ala Glu Val Phe Lys Ser Gly
                280                 285                 290 cac acc aca aat ggc atc tac acg tta aca ttc cct aat tct aca gaa     1270
His Thr Thr Asn Gly Ile Tyr Thr Leu Thr Phe Pro Asn Ser Thr Glu
            295                 300                 305 gag atc aag gcc tac tgt gac atg gaa gct gga gga ggc ggg tgg aca     1318
Glu Ile Lys Ala Tyr Cys Asp Met Glu Ala Gly Gly Gly Gly Trp Thr
        310                 315                 320
```

```
att att cag cga cgt gag gat ggc agc gtt gat ttt cag agg act tgg    1366
Ile Ile Gln Arg Arg Glu Asp Gly Ser Val Asp Phe Gln Arg Thr Trp
325                 330                 335 aaa gaa tat aaa gtg gga ttt ggt aac cct tca gga gaa tat tgg ctg    1414
Lys Glu Tyr Lys Val Gly Phe Gly Asn Pro Ser Gly Glu Tyr Trp Leu
340                 345                 350                 355 gga aat gag ttt gtt tcg caa ctg act aat cag caa cgc tat gtg ctt    1462
Gly Asn Glu Phe Val Ser Gln Leu Thr Asn Gln Gln Arg Tyr Val Leu
                360                 365                 370 aaa ata cac ctt aaa gac tgg gaa ggg aat gag gct tac tca ttg tat    1510
Lys Ile His Leu Lys Asp Trp Glu Gly Asn Glu Ala Tyr Ser Leu Tyr
        375                 380                 385 gaa cat ttc tat ctc tca agt gaa gaa ctc aat tat agg att cac ctt    1558
Glu His Phe Tyr Leu Ser Ser Glu Glu Leu Asn Tyr Arg Ile His Leu
    390                 395                 400 aaa gga ctt aca ggg aca gcc ggc aaa ata agc agc atc agc caa cca    1606
Lys Gly Leu Thr Gly Thr Ala Gly Lys Ile Ser Ser Ile Ser Gln Pro
405                 410                 415 gga aat gat ttt agc aca aag gat gga gac aac gac aaa tgt att tgc    1654
Gly Asn Asp Phe Ser Thr Lys Asp Gly Asp Asn Asp Lys Cys Ile Cys
420                 425                 430                 435 aaa tgt tca caa atg cta aca gga ggc tgg tgg ttt gat gca tgt ggt    1702
Lys Cys Ser Gln Met Leu Thr Gly Gly Trp Trp Phe Asp Ala Cys Gly
                440                 445                 450 cct tcc aac ttg aac gga atg tac tat cca cag agg cag aac aca aat    1750
Pro Ser Asn Leu Asn Gly Met Tyr Tyr Pro Gln Arg Gln Asn Thr Asn
        455                 460                 465 aag ttc aac ggc att aaa tgg tac tac tgg aaa ggc tca ggc tat tcg    1798
Lys Phe Asn Gly Ile Lys Trp Tyr Tyr Trp Lys Gly Ser Gly Tyr Ser
    470                 475                 480 ctc aag gcc aca acc atg atg atc cga cca gca gat ttc taa            1840
Leu Lys Ala Thr Thr Met Met Ile Arg Pro Ala Asp Phe *
485                 490                 495 acatcccagt ccacctgagg aactgtctcg aactattttc aaagacttaa gcccagtgca   1900
ctgaaagtca cggctgcgca ctgtgtcctc ttccaccaca gagggcgtgt gctcggtgct   1960
gacgggaccc acatgctcca gattagagcc tgtaaacttt atcacttaaa cttgcatcac   2020
ttaacggacc aaagcaagac cctaaacatc cataattgtg attagacaga acacctatgc   2080
aaagatgaac ccgaggctga aatcagact gacagtttac agacgctgct gtcacaacca    2140
agaatgttat gtgcaagttt atcagtaaat aactggaaaa cagaacactt atgttataca   2200
atacagatca tcttggaact gcattcttct gagcactgtt tatacactgt gtaaatacc    2260 atatgtcct                                                           2269

<210> SEQ ID NO 11
<211> LENGTH: 496
<212> TYPE: PRT
<213> ORGANISM: Homo sapiens

<400> SEQUENCE: 11

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60
```

-continued

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
                 85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln His Asp Leu Met Glu Thr Val Asn
                245                 250                 255

Asn Leu Leu Thr Met Met Ser Thr Ser Asn Ser Ala Lys Asp Pro Thr
                260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

-continued

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
            485                 490                 495

<210> SEQ ID NO 12
<211> LENGTH: 496
<212> TYPE: PRT
<213> ORGANISM: Homo sapiens

<400> SEQUENCE: 12

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
                20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

-continued

```
Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495
```